United States Patent
Sharkawy et al.

(10) Patent No.: US 7,232,449 B2
(45) Date of Patent: *Jun. 19, 2007

(54) COMPONENTS, SYSTEMS AND METHODS FOR FORMING ANASTOMOSES USING MAGNETISM OR OTHER COUPLING MEANS

(75) Inventors: A. Adam Sharkawy, Redwood City, CA (US); J. Greg Stine, San Jose, CA (US); David H. Cole, San Mateo, CA (US); Samuel Crews, Redwood City, CA (US); Darin C. Gittings, Sunnyvale, CA (US); Adam Kessler, Fremont, CA (US); Mark J. Foley, Menlo Park, CA (US)

(73) Assignee: Medtronic, Inc., Minneapolis, MN (US)

( * ) Notice: Subject to any disclaimer, the term of this patent is extended or adjusted under 35 U.S.C. 154(b) by 606 days.

This patent is subject to a terminal disclaimer.

(21) Appl. No.: 10/388,374

(22) Filed: Mar. 12, 2003

(65) Prior Publication Data

US 2004/0034377 A1    Feb. 19, 2004

Related U.S. Application Data

(63) Continuation-in-part of application No. 09/638,805, filed on Aug. 12, 2000, now Pat. No. 6,719,768, which is a continuation-in-part of application No. 09/562,599, filed on Apr. 29, 2000, now Pat. No. 6,352,543.

(60) Provisional application No. 09/851,400, filed on May 7, 2001, provisional application No. 60/255,635, filed on Dec. 13, 2000.

(51) Int. Cl.
    *A61B 17/08* (2006.01)

(52) U.S. Cl. .......... 606/153; 606/215; 128/898
(58) Field of Classification Search .......... 606/153, 606/213, 215; 623/1.13, 1.36, 1.1; 600/12; 128/898

See application file for complete search history.

(56) References Cited

U.S. PATENT DOCUMENTS 2,953,970 A    9/1960    Maynard (Continued)

FOREIGN PATENT DOCUMENTS

DE    29513195    12/1996

(Continued)

OTHER PUBLICATIONS

Esformes, et al., "Biological Effects of Magnetic Fields Generated with CoSm Magnets," pp. 81-87.

(Continued)

*Primary Examiner*—Julian W. Woo
(74) *Attorney, Agent, or Firm*—Mike Jaro; Jeffrey J. Hohenshell

(57) ABSTRACT

Anastomotic components may be attached to hollow bodies or vessels by magnetic or mechanical force to create an anastomosis, form a port in a vessel, or repair a diseased vessel lumen. Anastomoses are created by coupling a first connection to an end of a vessel and then attracting it to a second connector secured to the side wall of another vessel. The connection between the first and second connectors may be solidly magnetic, solely mechanical, or a combination thereof. Also disclosed are methods and devices for treating diseased vessel lumens, for example abdominal aortic aneurysm. A plurality of docking members is attached to the vessel at solicited positions, and then one or more grafts is secured to the docking members in any suitable manner.

9 Claims, 32 Drawing Sheets

U.S. PATENT DOCUMENTS

| | | | |
|---|---|---|---|
| 3,372,443 A | 3/1968 | Daddona, Jr. | |
| 3,727,658 A | 4/1973 | Eldridge, Jr. | |
| 3,952,334 A | 4/1976 | Bokros et al. | |
| 3,986,493 A | 10/1976 | Hendren, III | |
| 4,154,226 A | 5/1979 | Hennig et al. | |
| 4,210,132 A | 7/1980 | Perlin | |
| 4,233,981 A * | 11/1980 | Schomacher | 606/153 |
| 4,258,705 A | 3/1981 | Sorensen et al. | |
| 4,397,311 A | 8/1983 | Kanshin et al. | |
| 4,679,546 A | 7/1987 | Van Waalwijk van Doorn et al. | |
| 4,809,713 A | 3/1989 | Grayzel | |
| 4,837,114 A | 6/1989 | Hamada et al. | |
| 4,889,120 A | 12/1989 | Gordon | |
| 4,899,744 A | 2/1990 | Fujitsuka et al. | |
| 4,904,256 A | 2/1990 | Yamaguchi | |
| 4,917,778 A | 4/1990 | Takada et al. | |
| 4,935,080 A | 6/1990 | Hassell et al. | |
| 5,013,411 A | 5/1991 | Minowa et al. | |
| 5,275,891 A | 1/1994 | Tagaya et al. | |
| 5,316,595 A | 5/1994 | Hamada et al. | |
| 5,330,486 A | 7/1994 | Wilk | |
| 5,411,508 A | 5/1995 | Bessler et al. | |
| 5,425,763 A | 6/1995 | Stemmann | |
| 5,441,507 A | 8/1995 | Wilk | |
| 5,507,629 A | 4/1996 | Jarvik | |
| 5,595,562 A | 1/1997 | Grier | |
| 5,611,689 A | 3/1997 | Stemmann | |
| 5,690,656 A | 11/1997 | Cope et al. | |
| 5,695,504 A * | 12/1997 | Gifford et al. | 606/153 |
| 5,702,412 A | 12/1997 | Popov et al. | |
| 5,817,113 A | 10/1998 | Gifford, III et al. | |
| 5,830,224 A | 11/1998 | Cohn et al. | |
| 5,895,404 A | 4/1999 | Ruiz | |
| 5,904,147 A | 5/1999 | Conlan et al. | |
| 5,906,579 A | 5/1999 | Vander Salm et al. | |
| 5,997,467 A | 12/1999 | Connolly | |
| 6,068,637 A | 5/2000 | Popov et al. | |
| 6,074,416 A | 6/2000 | Berg et al. | |
| 6,099,542 A | 8/2000 | Cohn et al. | |
| 6,113,612 A | 9/2000 | Swanson et al. | |
| 6,173,715 B1 | 1/2001 | Sinanan et al. | |
| 6,190,353 B1 | 2/2001 | Makower et al. | |
| 6,352,543 B1 | 3/2002 | Cole | |
| 6,419,681 B1 | 7/2002 | Vargas et al. | |
| 6,565,581 B1 | 5/2003 | Spence et al. | |
| 6,575,168 B2 | 6/2003 | LaFontaine et al. | |
| 6,579,311 B1 | 6/2003 | Makower | |
| 6,932,827 B2 * | 8/2005 | Cole | 606/153 |
| 2002/0193782 A1 | 12/2002 | Ellis et al. | |
| 2003/0014061 A1 | 1/2003 | Houser et al. | |
| 2003/0014063 A1 | 1/2003 | Houser et al. | |
| 2003/0065345 A1 | 4/2003 | Weadock | |
| 2003/0167064 A1 | 9/2003 | Whayne | |

FOREIGN PATENT DOCUMENTS

| | | |
|---|---|---|
| DE | 29713335 | 7/1997 |
| RU | 2123300 | 12/1998 |
| SU | 736966 | 5/1980 |
| SU | 1025420 | 6/1983 |
| SU | 1179978 | 9/1985 |
| SU | 1438738 | 11/1988 |
| SU | 2018266 | 3/1989 |
| SU | 1537228 | 1/1990 |
| SU | 1595534 | 9/1990 |
| SU | 1629040 | 2/1991 |
| SU | 1635966 | 3/1991 |
| SU | 1277452 | 6/1991 |
| SU | 1708313 | 1/1992 |
| SU | 1361753 | 4/1992 |
| SU | 1725851 | 4/1992 |
| SU | 1766383 | 10/1992 |
| SU | 1769863 | 10/1992 |
| WO | WO 97/13463 | 4/1997 |
| WO | WO 97/27897 | 8/1997 |
| WO | WO 99/40851 | 8/1999 |
| WO | WO 99/62415 | 12/1999 |
| WO | WO 99/63894 | 12/1999 |
| WO | WO 00/09040 | 2/2000 |
| WO | WO 00/27312 | 5/2000 |
| WO | WO 00/32241 | 6/2000 |
| WO | WO 00/33770 | 6/2000 |
| WO | WO 00/69364 | 11/2000 |
| WO | WO 00/74579 | 12/2000 |
| WO | WO 01/39672 | 6/2001 |
| WO | WO 01/82803 | 11/2001 |
| WO | WO 02/09594 | 2/2002 |
| WO | WO 02/19946 | 3/2002 |
| WO | WO 02/39878 | 5/2002 |
| WO | WO 02/094108 | 11/2002 |

OTHER PUBLICATIONS

Fuestel, et al., "Kontinente Kolostomi durch Magnetverschluss," *Dtsch. Med. Wschr.* 100 (1975), pp. 1063-1064.

Obora, et al., "Nonsuture Microvascular Anastomosis Using Magnet Rings: Preliminary Report," *Surg. Neurol.*, vol. 9, Feb. 1978, pp. 117-120.

Kanshin, et al., "Sutureless anastomoses in gastrointestinal surgery with and without steady magnetic field," *Arkh Patol*, 1978; 40(8):5661. (English Abstract).

Pirusyan, et al., Some Regularities of Tissue Squeezing and Regeneration Under Formation of "Unstitch" Anastomoses of the Alimentary Canal's Hollow Organs, 1979, pp. 13-17). (Includes English abstract).

Obora, et al., "Nonsuture Microvascular Anastomosis using Magnetic Rings," Jan. 16, 1980, pp. 497-505. (English translation is provided.).

Yanase, "An Experimental Study on Traumatic Changes in Microvessels Produced by Pressure Clamping," *Aust N.Z. J. Surg.* vol. 50-No. 4, Aug. 1980, pp. 423-428.

Jansen, et al., "Clinical Applications of Magnetic Rings in Colorectal Anastomosis," *Surgery, Gynecology & Obstetrics*, vol. 153, Oct. 1981, pp. 537-545.

Myshkin, et al., "Use of Permanent Magnets in Sutureless Anastomoses," 1987, pp. 47-52. (English translation is provided.).

Kanshin, et al., "A Goal-Oriented Local Approach to the Prevention of Postoperative Purulent Complications," 1991, pp. 24-27. (English abstract is provided.).

Stepanov, et al., "The treatment of intestinal fistulae in children by applying a bypass anastomosis using magnetic devices," *Khirugiia (Mosk)*, Nov.-Dec. 1992, pp. 11-12. (English abstract is provided.).

Fukumura, et al., "Development of a Magnetically Operated Artificial Urethral Sphincter," *ASAIO Journal*, 1993, pp. M283-M287.

Bondemark, et al., "Orthodontic Rare Earth Magnets—In Vitro Assessment of Cytotoxicity," *British Journal of Orthodontia*, vol. 21, No. 4, Nov. 1994, pp. 335-341.

Cope, "Evaluation of Compression Cholecystogastric and Cholecystojejunal Anastomoses in Swine after Peroral and Surgical Introduction of Magnets," *Journal of Vascular and Interventional Radiology*, vol. 6, No. 4, Jul.-Aug. 1995, pp. 546-552.

Cope, "Creation of Compression Gastroenterostomy by Means of the Oral, Percutaneous, or Surgical Introduction of Magnets: Feasibility Study in Swine," *Journal of Vascular and Interventional Radiology*, vol. 6, No. 4, Jul.-Aug. 1995, pp. 539-545.

Bondemark, et al., "Long-term effects of orthodontic magnets on human buccal mucosa—a clinical, histological and immunohistochemical study," *Eur J Orthod.*, 20(3), Jun. 1998, pp. 211-218.

Cope, "Stent Placement of Gastroenteric Anastomoses Formed by Magnetic Compression," *Journal of Visceral Intervention*, vol. 10, No. 10, Nov.-Dec. 1999, pp. 1379-1386.

Ahn CY, Shaw WW, Berns S, et al., "Clinical Experience With the 3M Microvascular Coupling Anastomotic Device in 100 Free-Tissue Transfers," *Plastic and Reconstructive Surgery*, Jun. 1994; 93(7):1481-84.

Bjork VO, Iert T, Landou C., "Angiographic changes in Internal Mammary Artery and Saphenous Vein Grafts, Two Weeks, One Year and Five Years After Coronary Bypass Surgery," *Scand J Thor Cardiovasc Surg*, 1981; 15:23-30.

Bornemisza G, Furka I., "Nonsuture Vascular Anastomosis," *Acta Chirurgica Academiae Scientiarium Hungaricae, Tomus*, 1971; 12(1):49-56.

Bourassa MG, Fisher LD, Campeau L, et al., "Long-Term Fate if Bypass Grafts: The Coronary Artery Surgery Study (CASS) and Montreal Heart Institute Experiences," *Circ*, Dec. 1985; 72(suppl V):71-77.

Buffolo E, de Andrade JCS, Branco JNR, et al., "Corornary Artery Bypass Grafting Without Cardiopulmonary Bypass," *Ann Thorac Surg*, 1996; 61:63-6.

Casanova R, Herrera GA, Vasconez EB, et al, "Microarterial Sutureless Sleeve Anastomosis Using a Polymeric Adhesive: An Experimental Study," *J Reconstr Microsurg*, Apr. 1987; 3(3):201-7.

David JL, Limet R, "Antiplatelet Activity of Clopidogrel in Coronary Artery Bypass Graft Surgery Patients," *Thromb Haemost*, Nov. 1999; 82(5):417-21.

DeLacure MD, Kuriakose MA, Spies AL, "Clinical Experience in End-to-Side Venous Anastomosis With a Microvascular Anastomotic Coupling Device in Head and Neck Reconstruction," *Arch Otolaryngol Head Neck Surg*, Aug. 1999; 125:869-72.

Detweiler MB, Detweiler JG, Fenton J, et al., "Sutureless and Reduced Suture Anastomosis of Hollow Vessels with Fibrin Glue: A Review," *J Invest Surg*, Sep. 1999; 12(5):245-62.

Eckstein FS, Bonilla LF, Meyer B, et al., "Sutureless mechanical anastomosis of a saphenous vein graft to a coronary artery with a new connector device," *Lancet*, vol. 357, Mar. 24, 2001, pp. 931-932.

Frey RR, Bruschke AVG, Vermeulen FEE, "Serial Angiographic Evaluation 1 Year and 9 Years After Aorata-Coronary Bypass," *J Thorac Cardiovasc Surg*, 1984; 87(2):167-74.

Goldman S, et al., "Starting aspirin therapy after operation—effects on early graft patency," *Circulation*, 1991; 84:520.

Goldman S, Copeland J, Moritz T, et al., "Improvement in Early Saphenous Vein Graft Patency After Coronary Artery Bypass Surgery With Antiplatelet Therapy: Results of a Veterans Administration Cooperative Study," *Circulation*, Jun. 1988; 77(6):1324-32.

Goldman S, Zadina K, Krasnicka B, et al., "Predictors of Graft Patency 3 Years After Coronary Artery Bypass Graft Surgery," *J Am Coll Cardiol*, Jun. 1997; 29(7):1563-8.

Goy JJ, Kaufman U, Goy-Eggenberger D, et al., "A Prospective Randomized Trial Comparing Stenting to Internal Mammary Artery Grafting for Proximal, Isolated de novo Left Anterior Coronary Artery Stenosis: The SIMA Trial, *Stenting* vs. *Internal Mammary Artery*," *Mayo Clin Proc*, Nov. 2000; 75(11):1116-23.

Gundry SR, Black K, Izuntani H, "Sutureless Coronary Artery Bypass with Biologic Glued Anastomosis: Preliminary In Vivo and In Vitro Results," *J Thorac Cardiovasc Surg*, Sep. 2000; 120(3):473-77.

Guyton RA, McClenathan JH, Michaelis LL, "A Mechanical Device for Sutureless Aorta-Saphenous Vein Anastomosis," *Ann Thorac Surg*, Oct. 1979; 28(4):342-5.

Heijmen RH, Borst C, van Dalen R, et al., "Temporary Luminal Arteriotomy Seal: II. Coronary Artery Bypass Grafting on the Beating Heart," *Ann Thorac Surg*, 1998; 66:471-6.

Heijmen RH, Hinchliffe P, Borst C, et al., "A Novel One-Shot Anastomotic Stapler Prototype for the Coronary Bypass Grafting on the Beating Heart: Feasibility on the Pig," *J Thorac and Cardiovasc Surg*, Jan. 1999; 117(1):117-25.

Lytle BW, Loop FD, Cosgrove DM, et al., "Long-Term (5 to 12 Years) Serial Studies of Internal Mammary Artery and Saphenous Vein Coronary Bypass Grafts." *J Thorac and Cardiovasc Surg*, Feb. 1985; 89(2):248-58.

Mattox DE, Wozniak JJ, "Sutureless Vascular Anastomosis with Biocompatible Heat-Shrink Tubing," *Arch Otolaryngol Head Neck Surg*, Nov. 1991; 117:1260-4.

Nataf P, Kirsch W, Hill AC, et al., "Nonpentrating Clips for Coronary Anastomosis," *Ann Thorac Surg*, 1997; 63:S135.

Nataf P, Hinchliffe P, Manzo S, et al., "Facilitated Vascular Anastomoses: The One-Shot Device," *Ann Thorac Surg*, 1998; 66:1041.

Paz MA, Lupon J, Bosch X, et al., "Predictors of Early Saphenous Vein Aortocoronary Bypass Graft Occlusion. The GESIC Study Group," *Ann Thorac Surg*, Nov. 1993; 56(5):1101-6.

Puskas JD, Wright CE, Ronson RS, et al., "Clinical Outcomes and Angiographic Patency in 125 Consecutive Off-Pump Coronary Bypass Patients," *The Heart Surgery Forum #999-95310*, May 1999; 2(3):216-21.

Rueland D, Schomacher PR, Mueller KM, et al., "Experimental Studies With a New Sutureless Anastomic Flange," *Trans AM Soc Artif Intern Organs*, 1979; 25:339-43.

Sanz G, Pajaron A, Algria E, et al., "Prevention of Early Aortocoronary Bypass Occlusion by Low-Dose Aspirin and Dipyridamole," *Circulation*, Sep. 1990; 82(3):765-72.

Scheltes JS, Heikens M, Pistecky PV, et al., "Assessment of Patented Coronary End-to-Side Anastomotic Devices Using Micromechanical Bonding," *Ann Thorac Surg*, Jul. 2000; 70(1):218-21.

Seides SF, Borer JS, Kent KM, et al., "Long-Term Anatomic Fate of Coronary-Artery Bypass Grafts and Functional Status of Patients Five Years after Operation," *N Engl J Med*, 1978; 298(22):1213-17.

Sethi GK, Copeland JG, Goldman S, et al., "Implications of Preoperative Administration of Aspirin in Patients Undergoing Coronary Artery Bypass Grafting. Department of Veterans Affairs Cooperative Study on Antiplatelet Therapy," *J Am Coll Cardiol*, Jan. 1990; 15(1):15-20.

Souza DSR, Bomfim V, Skoglund H, et al., "High Early Patency Saphenous Vein Graft for Coronary Artery Bypass Havested with Surrounding Tissue," *Ann Thorac Surg*, 2001; 71:797-800.

Takenaka H, Esato K, Ohara M, et al., "Sutureless Anastomosis of Blood Vessels Using Cyanoacrylate Adhesives," *Surg Today*, 1999; 22(1):46-54.

Werker P, Kon M, "Review of Facilitated approaches to Vascular Anastomosis Surgery," *Ann Thorac Surg*, 1997; 63:S122.

Weissberg D, Schwartz P, Goetz RH, Nonsuture End-to-Side Anastomoses of Small Blood Vessels, *Surgery, Gynecology & Obstetrics*, Aug. 1966; 341-46.

Whiffen JD, Boake WC, Gott VL, "Vessel Patency Following Nonsuture Anastomosis with Intravascular Rings," *Arch Surg*, Dec. 1965; 91(6):939-41.

Yamagata S, Carter LP, Handa H, et al., "Experimental Studies in Nonsuture End-to-Side Microvascular Anastomosis," *Neurol Med Chiro* (Tokyo), 1981; 21:701-08.

Zegdi R, Martinod E, Fabre O, et al., "Video-Assisted Replacement of Bypass Grafting of the Descending Thoracic Aorta With a New Sutureless Vascular Prostahesis: An Experimental Study," *J Vasc Surg*, 1999; 30:320-4.

Evans RD, et al., "Effect of Corrosion Products (neodymium Iron Boron) on Oral Fibroblast Proliferation," *J of Applied*, 1995; 6(3):199-202.

Pourbaix M, "Electrochemical Corrosion of Metallic Biomaterials," *J of Applied Biomaterials*, 1984; 5:122-134.

Kitsugi A, et al., "The Corrosion Behavior of Nd2Fe14B and SmCo5 Magnets," *Dental Materials Journal*, 1992; 11(20):119-29.

Ku NC, et al., "Enhanced corrosion Resistance of NdFeB Type Permanent Magnet Coated by a Dual Layer of Either Ti/Al or Ni/Al Intermetallics," *IEEE Transactions on Magnetics*, 1997; 33(5):3913-5.

Cheng CW, et al., "Magnetic and Corrosion Characteristics of Nd-Fe-B Magnet with Various Surface Coatings," *IEEE Transactions on Magnetics*, 1997; 33(5):3910-3912 and CD-10.

Senftle F, et al., "Electrolytic Corrosion of Gold and the Formation of Au2(SO4)3 in Concentrated Sulfuric Acid," *Journal of the Electrochemical Society*, 1985; 129-30.

Thierry B, et al., "Effect of Surface Treatment and Sterilization Processes on the Corrosion Behavior of NiTi Shape Memory Alloy," *JBMR*, 51(4), 2000; 685-93.

Ryhanen J, et al., "Biocompatibility of Nickel-Titanium Shape Memory Metal and Its Corrosion Behavior in Human Cell Cultures," *JBMR*, 33 1997; 451-7.

Endo K, et al., "Effects of Titanium Nitride Coatings on Surface and Corrosion Characteristics on Ni-Ti Alloy," *Dental Materials Journal*, 1994; 13(2):228-39.

Angelini E, et al., "Corrosion under Static and Dynamic Conditions of Alloys Used for Magnetic Retention in Dentistry," *J Prosthet Dent*, 1991; 65:848-53.

Willman CJ, et al., "Corrosion Characteristics of RE-Fe-B Permanent Magnets," *J Appl Phys*, 1987; 61(8):3766-3768.

Attanasio SA, et al., "Corrosion of Rapidly Solidified Neodymion-Iron-Boron (Nd-Fe-B) Permanent Magnets and Protection via Sacrificial Zinc Coatings," *Material Science and Engineering*, 1995; A198:25-34.

Bala H, et al., "Effect of Impurities on the Corrosion Behavior of Neomydium," *Journal of Applied Electrochemistry*, 1993; 23(10):1017-1024.

Grieb B, "New Corrosion Resistant Materials Based on Neodym-Iron-Boron," *Intermag Conference*, 1997; CD-08.

Konerding MA, et al., "Scanning Electron Microscopy of Corrosion Casting in Medicine," *Scanning Microscopy*, 1991; 5(3):851-865.

Lamestschwandter A, et al., "Scanning Electron Microscopy of Vascular Corrosion Casts—Technique and Applications: Updated Review," *Scanning Microscopy*, 1990; 4(4):889-941.

Aharinejad S.H., et al., *Microvascular Corrosion Casting in Scanning Electron Microscopy. Technique and Applications*, Springer—Verlag/Wien, New York, pp. 12-23, 25, 28-39, 63-73, 75-81.

Cheng CW, Cheng FT, Man HC, "Improvement of protective coatings on Nd-Fe-B magnet by pulse nickel plating," *Journal of Applied Physics*, Jun. 1, 1998; 83(11):6417-6419.

Minowa T, Yoshikawa M, Honshima M, "Improvement of the corrosion resistance on Nd-Fe-B magnet with nickel plating," *IEEE Transactions on Magnetics*, Sep. 1989; 25(5):3776-3778.

Ku NC, Qin C-D, Yu CC and Ng DHL, "Corrosion Reisstance of NdFeB magnets coated by Al," *IEEE Transactions on Magnetics*, Sep. 1996; 32(5):4407-4409.

Dormer KJ, Gan RZ, Santo R, "Middle Ear Titanium Transducer," *Society for Biomaterials*, Sixth World Biomaterials Congress Transactions; 2000: 1272.

Noar JH, Whab A, Evans RD, Wojcik AG, "The durability of parylene coatings on neodymium-iron-boron magnets," *Eur J Orthod,*, Dec. 1999; 21(6):685-93.

Riess, Friedrich-Christian, et al., "Clinical Experience with the CorLink Device for Proximal Anastomosis of the Saphenous Vein to the Aorata: A Clinical Prospective, and Randomized Study," *The Heart Surgery Forum*, #2002-71002, 5(4), 2002:345-353.

Magnet Sales and Manufacturing Company, Inc., "Neodymium Iron Boron," Website: www.magnetsales.com, 4 pages (2000).

Group Arnold, The Magnetic Products Group of SPS Technologies, "Neodymium Magnets," Website: www.grouparnold.com, 2 pages (2000).

Brochure for "Neomax, Rare Earth Magnets," pp. 31-33, undated.

Sugiura T., "Magnetic Compression Anastomosis of the Vascular System in Experimental Dog Models," 211, p. S141, 1 page English abstract and 12 page slide show.

* cited by examiner

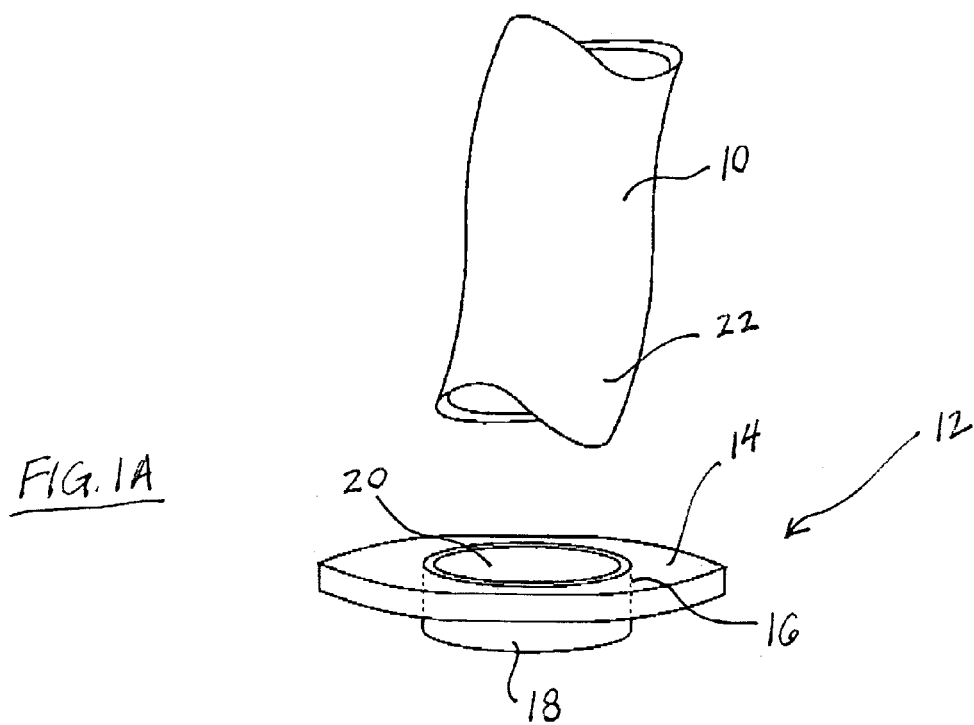
FIG. 1A
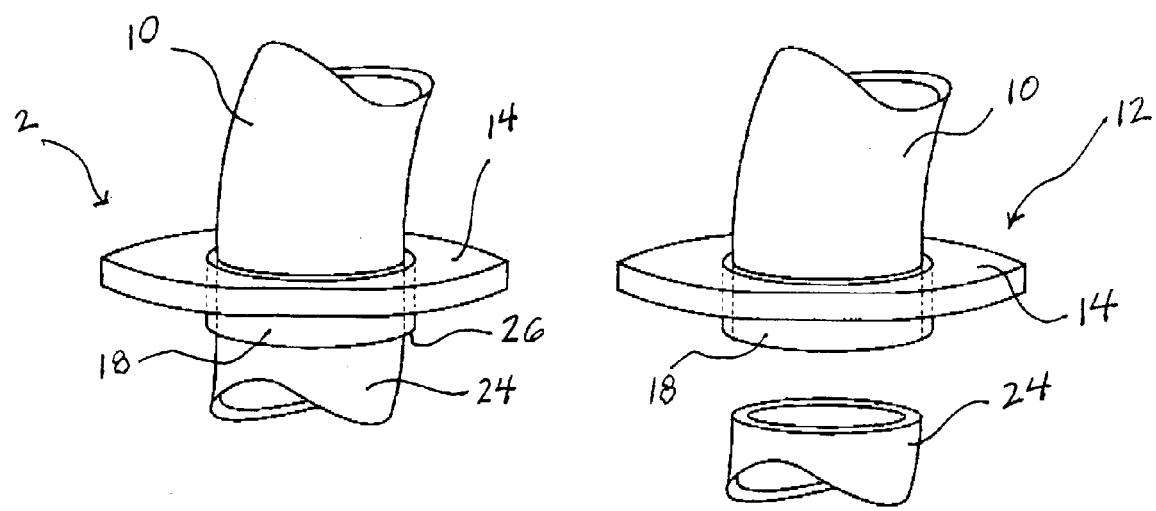
FIG. 1B
FIG. 1C

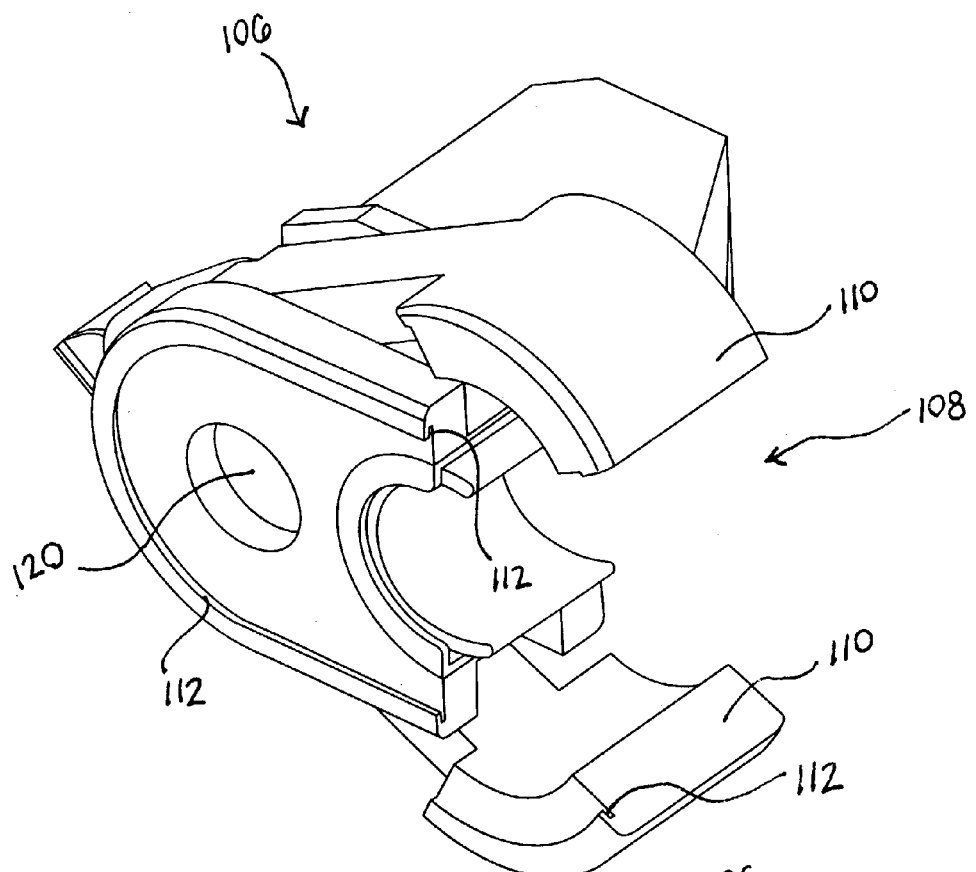
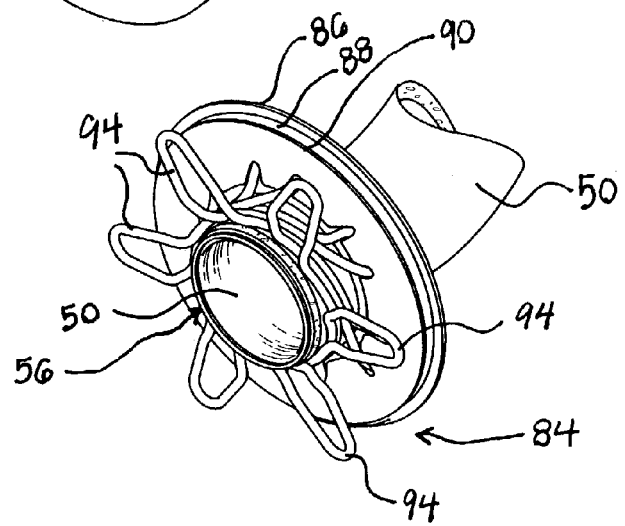
FIG. 16

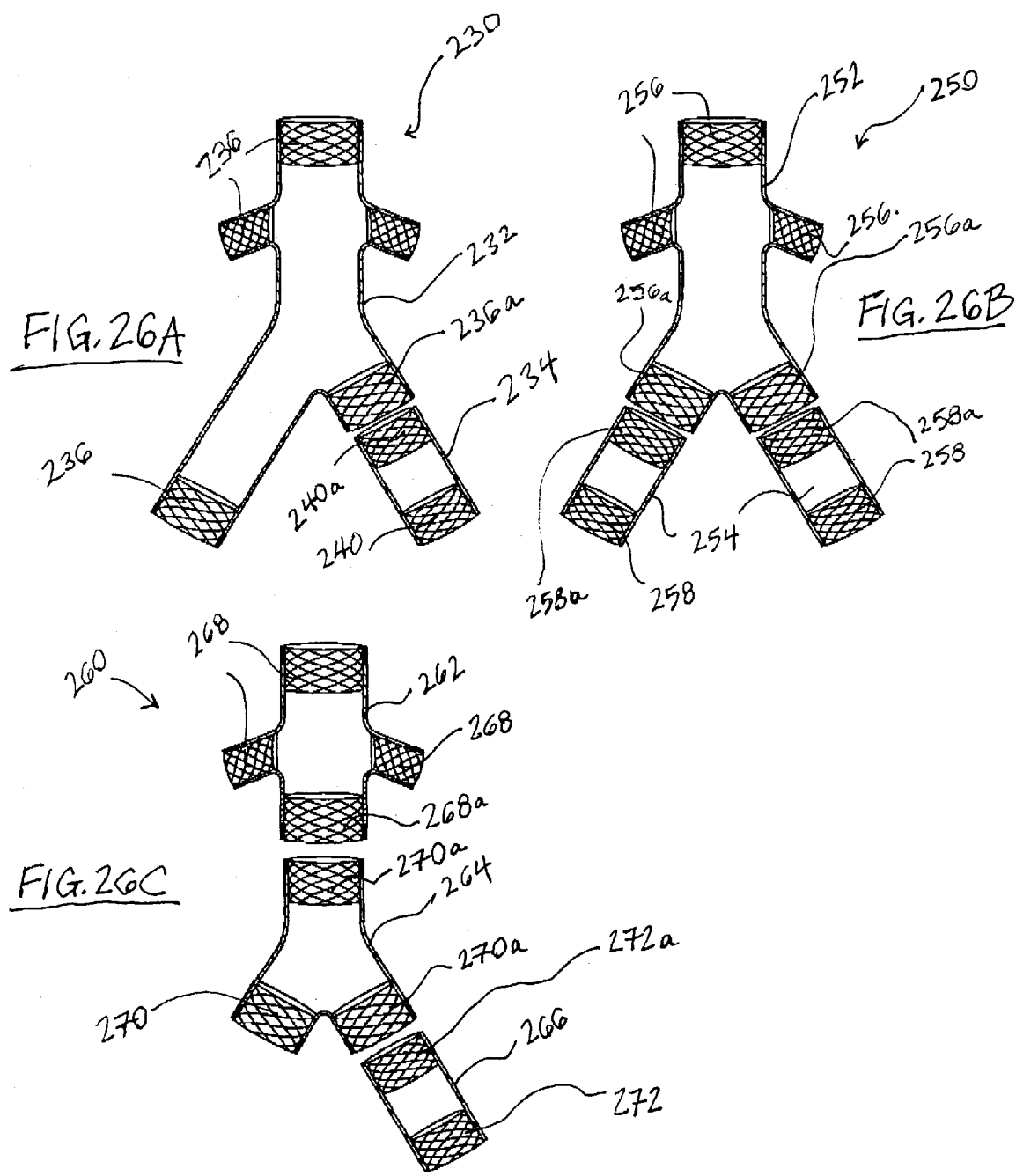

COMPONENTS, SYSTEMS AND METHODS FOR FORMING ANASTOMOSES USING MAGNETISM OR OTHER COUPLING MEANS

CROSS-REFERENCE TO RELATED APPLICATIONS

The present application is a continuation-in-part of application Ser. No. 09/638,805, filed Aug. 12, 2000 now U.S. Pat. No. 6,719,768, which is a continuation-in-part of application Ser. No. 09/562,599, filed Apr. 29, 2000, now U.S. Pat. No. 6,352,543. This application also claims priority from provisional application Ser. No. 60/255,635, filed Dec. 13, 2000, and application Ser. No. 09/851,400, filed May 7, 2001. The entire disclosure of each of the above-referenced patent applications is expressly incorporated herein by reference.

BACKGROUND OF THE INVENTION

1. Field of the Invention

The invention relates to treating hollow anatomical structures having a lumen. More specifically, the invention relates to treating one or more diseased body lumens, creating anastomoses between such hollow body structures, and using magnetism to secure anastomotic components to such structures, for example, in conjunction with creating an anastomosis.

2. Description of Related Art

Despite the considerable advances that have been realized in both interventional cardiology and cardiovascular surgery, heart disease remains the leading cause of death throughout much of the world. Coronary artery disease, or arteriosclerosis, is the single leading cause of death in the United States today. As a result, those in the cardiovascular field continue to search for new treatments and improvements to existing treatments.

Coronary artery disease is currently treated by interventional procedures such as percutaneous transluminal coronary angioplasty (PTCA), coronary stenting and atherectomy, as well as surgical procedures including coronary artery bypass grafting (CABG). The goal of these procedures is to reestablish or improve blood flow through occluded (or partially occluded) coronary arteries, and is accomplished, for example, by enlarging the blood flow lumen of the artery or forming a bypass that allows blood to circumvent the occlusion. What procedure(s) is used typically depends on the severity and location of the blockage. When successful, these procedures restore blood flow to myocardial tissue that had not been sufficiently perfused due to the occlusion.

Another proposed treatment places the target vessel, e.g., a coronary artery, in direct fluid communication with a heart chamber containing blood, for example, the left ventricle. Blood flows from the ventricle into a conduit that is in fluid communication with the artery; as such, this treatment may be described as a ventricular bypass procedure. Benefits of this procedure include obviating the need to manipulate the aorta, for example, as is done when a side-biting clamp is used in a typical CABG procedure to create a proximal anastomosis between the bypass graft and the aorta. Clamping or otherwise manipulating the aorta places the patient at risk in some cases due to the likelihood that such manipulation will release embolic material into the bloodstream. Some challenges associated with this procedure include delivering and deploying the conduit in the patient's body in proper position with respect to the heart chamber and the coronary vessel.

A particularly challenging task that must be performed during many of these and other revascularization procedures is suturing one hollow structure to another hollow structure. For instance, one end of a graft vessel is sutured to a source of blood, such as the aorta, a heart chamber or another blood vessel, while another end of the graft vessel is sutured to a target vessel, such as a coronary artery having an occluded lumen. The small diameter of the hollow structures involved, typically from 1 mm to 4 mm, makes forming a handsewn anastomosis a highly technical and time-consuming procedure. The difficulty in forming the sutured anastomosis is exacerbated when access to the target vessel is restricted or limited, as in a minimally invasive or percutaneous procedure. This problem can also arise in non-cardiovascular applications that utilize handsewn anastomoses, for example, treating peripheral vascular disease or injury, creating AV (arteriovenous) shunts, etc.

While those in the art have proposed various anastomotic coupling, none has performed well enough to receive any significant level of acceptance in the field. Many of the proposed couplings penetrate or damage the wall of the hollow structures, do not remain patent, fail to produce a fluid-tight seal between the conduit and vessel, or are simply too cumbersome and difficult to deliver or deploy.

It should be noted, though, that a more recently proposed technology which uses magnetism to treat hollow anatomical structures has enjoyed clinical success in creating an anastomosis between a graft blood vessel and a coronary artery. This anastomotic technology, which was developed by Ventrica, Inc., of Fremont, Calif., and is referred to as the MVP™ (Magnetic Vascular Positioner) anastomotic system, provides considerable benefits over other proposed technologies. Nevertheless, there remains room in the art for improvement with respect to a number of technological and procedural areas.

For example, it is desirable to maximize the ability of the technology to be used in a minimally invasive manner, such as in a procedure performed by a robotic system. As another example, it is desirable to minimize the amount of foreign material in the blood flow path so as to decrease the chance of thrombosis. Achieving this goal, however, must be balanced with the need to form a secure connection between the anastomotic components, or between a component and a hollow body structure.

SUMMARY OF THE INVENTION

One embodiment of the invention provides a method for forming an anastomosis between two blood vessels using magnetism and includes steps of securing a first component to a first blood vessel and securing a second component to a side wall of a second blood vessel in alignment with an opening in the side wall. Further steps include placing the first component in contact with at least one of the second component and the side wall of the second blood vessel, positioning an intimal surface of the first blood vessel adjacent an intimal surface of the second blood vessel, and using magnetism to couple the first and second components.

Another embodiment of the invention provides a method for forming an anastomosis between two blood vessels with steps of securing a first component to an end portion of a first blood vessel securing a second component to a side wall of a second blood vessel with an opening in the second component substantially aligned with an opening in the side wall, placing the first component and the end portion of the first blood vessel through the opening in the second component and the opening in the side wall of the second blood vessel, and coupling the first and second components to form an anastomosis between the first and second blood vessels.

Another embodiment of the invention provides a method with steps of providing an anastomotic component including a sleeve defining a lumen, securing an end portion of a blood vessel to the anastomotic component by passing the end portion through the sleeve, placing an edge of the blood vessel in substantial alignment with an edge of the anastomotic component, and passing a fastener through the end portion of the blood vessel and into locking engagement with the sleeve, the fastener leaving an exposed intimal surface that extends substantially around the sleeve.

Another embodiment of the invention provides a method for securing an anastomotic component to a side wall of a blood vessel and has steps of providing an anastomotic component including a non-expandable portion and an expandable portion, the anastomotic component comprising a wire shaped to define a lumen and multiple tissue engaging portions, forming an opening in a side wall of a blood vessel, collapsing the expandable portion of the anastomotic component by collapsing the wire, expanding the expandable portion of the anastomotic component by expanding the wire, and securing the anastomotic component to the blood vessel by engaging the tissue engaging portions with the vessel side wall.

Another embodiment of the invention provides a method for treating a lumen defined by a hollow structure in a patient's body and includes steps of providing a docking member configured to be secured to tissue, providing a prosthesis configured to be magnetically coupled to the docking member, the prosthesis having a lumen, securing the docking member to a vessel in a patient's body, the vessel having a lumen with a diseased portion, and magnetically coupling the prosthesis to the docking member to place the prosthesis lumen in sealing engagement with the vessel lumen.

Still another embodiment of the invention provides a method for repairing an aneurysm located in a patient's body lumen and includes steps of providing a prosthesis having an outer surface and a lumen, locating a body lumen having an aneurysm, placing the prosthesis in a desired position with respect to the aneurysm so that the prosthesis lumen sealingly engages the body lumen, and using magnetism to secure the prosthesis in the selected position.

Yet another embodiment of the invention provides an anastomotic component including a sleeve having a lumen adapted to receive a first vessel, and a plate extending away from the sleeve, the plate having an opening communicating with the sleeve lumen wherein at least one of the sleeve and plate includes a locking portion configured to lockingly engage another anastomotic component secured to a second vessel.

BRIEF DESCRIPTION OF THE DRAWING FIGURES

Other features, benefits and advantages of the invention will become apparent from the following detailed description of preferred embodiments thereof, taken in conjunction with the accompanying Figures, wherein:

FIGS. 1A–1C are sequential perspective views showing a vessel being attached to an anastomotic component according to one embodiment of the invention;

FIG. 16 shows the delivery device opened to release the now-coupled first and second anastomotic components.

FIGS. 26A–26C are elevation views, in section, of lumen repair devices constructed according to the other embodiments of the invention;

DETAILED DESCRIPTION OF PREFERRED EMBODIMENTS

Figure 2A:
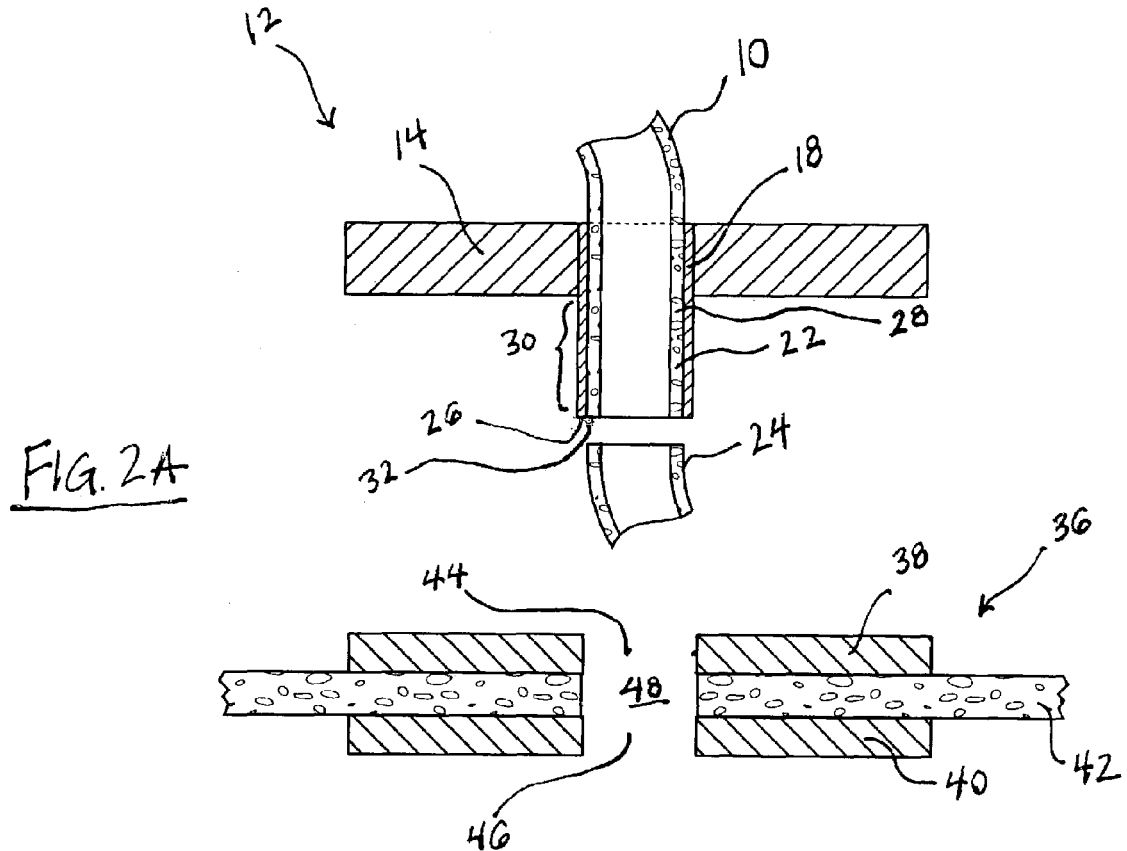
FIGS. 2A–2B are sectional views corresponding to FIGS. 1A and 1C, wherein a second anastomotic component provided on a target vessel is coupled to the anastomotic component shown in FIG. 1A.

With reference to FIGS. 1A–1C, a first embodiment of the invention is shown alongside a first vessel, organ, or part thereof, indicated by reference numeral 10. The various embodiments may be used to form an anastomosis between vessels, organs, or any anatomical structure having a lumen, for example. The invention also encompasses devices and methods for repairing a diseased body lumen.

It will be appreciated that the invention has applications beyond the specific uses mentioned above. Additional exemplary applications for the invention are disclosed in the aforementioned priority applications, the entire subject matter of each application being expressly incorporated herein by reference.

A first anastomotic component 12 comprises a body which, in the illustrated embodiment, is an annular member 14 having an opening 16. The anastomotic component 12 also includes a sleeve 18 with a lumen 20 (FIG. 1A). An end portion 22 of the first vessel 10 is passed through the lumen 20 of the sleeve 18 (FIG. 1B), and a portion 24 of the vessel 10 that extends beyond the sleeve 18 is trimmed even with the sleeve end 26 (FIG. 1C). It will be appreciated that the first vessel 10 and the anastomotic component 12 may be secured in a different relative position than that shown in FIG. 1C. For example, the end of the vessel 10 may extend beyond and be everted (not shown) over the end 26 of the sleeve 18.

The vessel 10 may be attached to the anastomotic component 12, and preferably the sleeve 18, by any suitable means, e.g., adhesive, staples, clips, pins, suture, etc. FIG. 2A shows the first anastomotic component 12 secured to the first vessel 10. As can be seen, a portion 28 of the vessel 10 extends along the length of the sleeve 18. In this embodiment, the exterior of the vessel portion 28 is partially or entirely adhesively secured to the inner surface of the sleeve 18. A portion 30 of the sleeve 18 extends beyond the annular member 14 and terminates at the vessel end 32. This exposes an intimal surface 32 of the first vessel 10 at the end 26 of the sleeve 18 of the component 12 (FIG. 2A).

FIG. 2A also shows a second anastomotic component 36 positioned next to the first component 12. The second component 36 comprises a pair of annular members 38, 40, disposed on opposite surfaces of the wall of a second vessel 42. In this embodiment, magnetic force secures the second component members 38, 40 to the second vessel 42; magnetic force also secures the first and second anastomotic components 12, 36 together to form the anastomosis. It should be recognized that magnetic force or nonmagnetic force (or a combination of the two) may be used to secure one or both anastomotic components to a respective vessel, or to couple the two components together to place the vessels in communication.

Figure 2B:
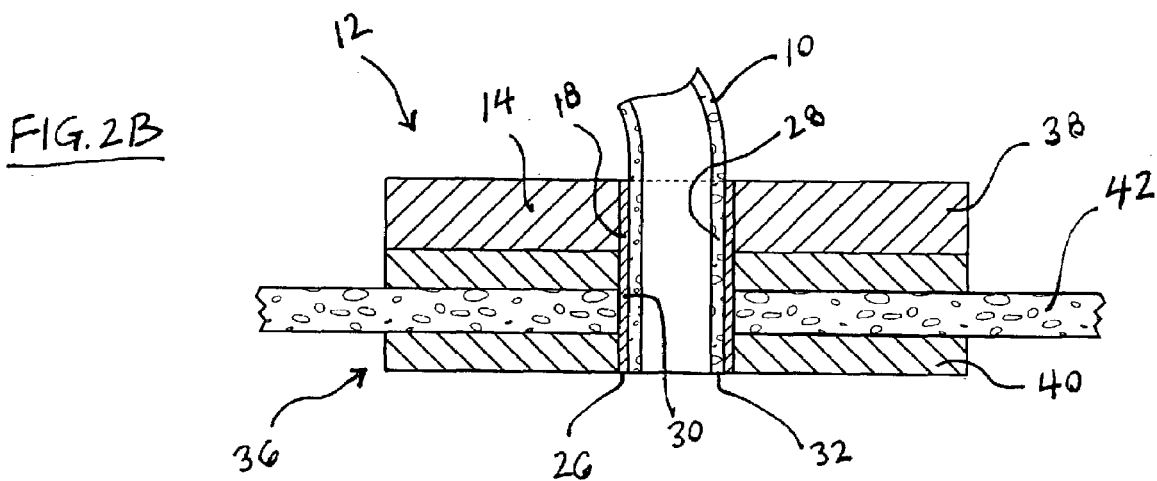

As seen in FIG. 2A, the members 38, 40 of the second component have respective openings 44, 46 that are aligned with an opening 48 in the wall of second vessel 42. The first anastomotic component 12 is magnetically coupled to the second anastomotic component 36, with the annular member 14 engaging the annular member 38 (FIG. 2B). The extended portion 30 of the sleeve 18 is positioned through the openings 44, 46 of the second component members 38, 40 and through the opening 48 in the side wall of the second vessel 42. The first and second components 12, 36 are preferably sized and configured to leave a relatively small amount of foreign material in the blood flow path. In this embodiment, essentially only the material of the second component member 40 is exposed to blood, as shown in FIG. 2B. Minimizing the amount of foreign material in the blood flow path is desirable because it decreases the possibility of thrombosis and thus improves patency of the anastomotic connection.

In the illustrated embodiment, the thickness T1 of the second component, including the thickness of the second vessel wall 42, is equal (or approximately equal) to the length L1 of the extended portion 30 of the first component 12. As a result, as shown in FIG. 2B, the end 26 of the sleeve 18 and the intimal surface 32 of first vessel 10 are substantially flush with the inner surface of the annular member 40. This configuration allows the first vessel 10 to extend only through the members 38, 40 and the second vessel wall 42, thereby removing the members 38, 40 from the blood flow path.

As noted above, magnetic or nonmagnetic force may be used to secure the anastomotic components of the invention to a selected vessel. With reference to FIG. 3A through FIG. 4B, an embodiment using a mechanical, nonmagnetic attachment will be described.

Figure 3A:
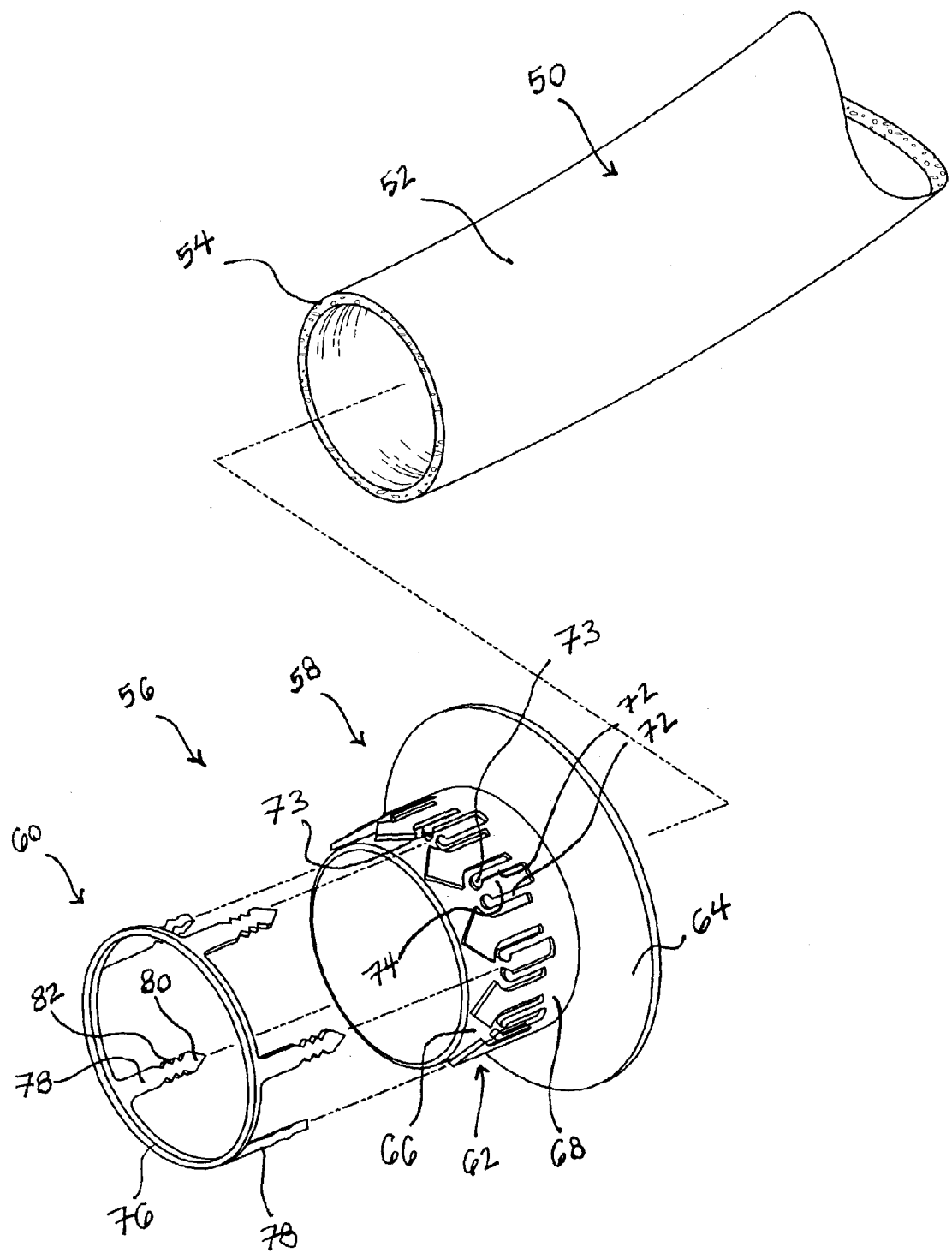
FIG. 3A is an exploded perspective view of a vessel and an anastomotic component constructed according to another embodiment of the invention.
Figure 3B:
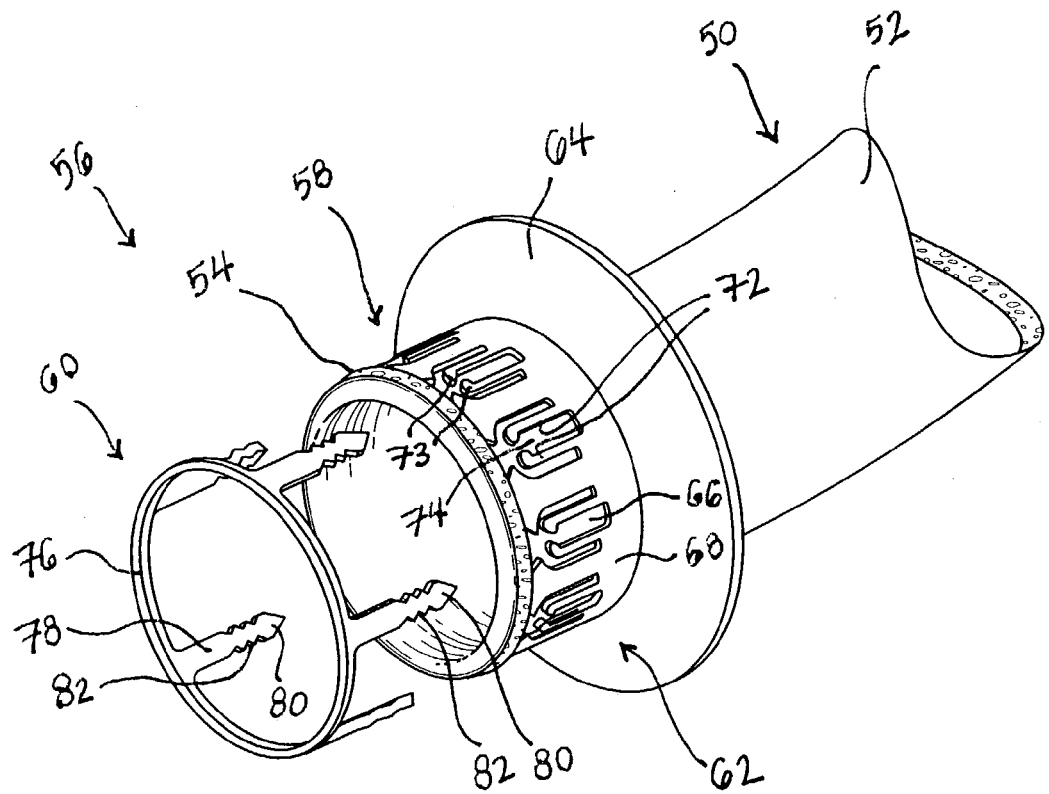
FIGS. 3B and 3C show the anastomotic component of FIG. 3A being attached to the end of the vessel.
Figure 3C:
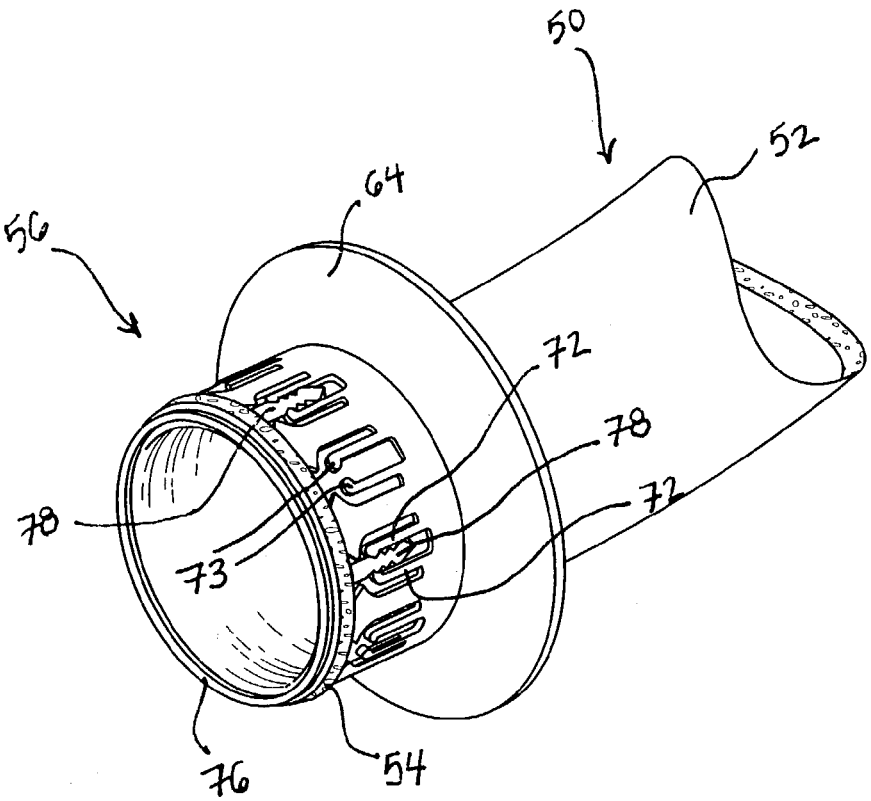

FIGS. 3A–3C show a first vessel 50 having a sidewall 52 and an end 54. An anastomotic component 56 comprises a base 58 and a locking member for securing the base 58 to the vessel 50. In the illustrated embodiment, the locking member is in the form of a fastener 60. The fastener 60 and the base 58 are configured to lock together, preferably in any of a plurality of positions, so as to attach the vessel 50 to the base 58.

Referring to FIG. 3A, the base 58 comprises a collar 62 extending from an annular plate 64. The illustrated collar 62 has multiple layers, namely, an inner sleeve 66, a middle sleeve 68 and an outer sleeve (omitted from FIGS. 3A–3C for clarity, but designated by reference numeral 70 in FIGS. 4A and 4B). The inner sleeve 66 is sized and configured to receive the vessel 50. The middle sleeve 68 is configured to lockingly engage the fastener 60. The outer sleeve 70 provides a cover and, preferably, means (FIGS. 4A and 4B) for securing the anastomotic component 56 to another anastomotic component (not shown).

The middle sleeve 68 of the collar 62 has a plurality of paired arms 72, each pair defining a space 74. The fastener 60 comprises a base 76 and a plurality of prongs 78 configured to enter the spaces 74. Each prong 78 has an end 80 and multiple locking elements 82. The locking elements 82 carried by the prongs 78 engage the ends 73 of the arms 72 to lock the fastener 60 to the base 58. It will be appreciated that the specific manner of locking the base 58 and fastener 60 together may be different from that shown. As an example, rather than using an integrally formed fastener with several prongs 78, a plurality of individual, discrete prongs (e.g., staples) could be used to secure the base 58 to the vessel 50.

The manner in which the first anastomotic component 56 is secured to the vessel 50 will now be described. The end 54 of the vessel 50 is passed through the bore of the plate 64 and the inner sleeve 66 to a position adjacent the end of the collar 62. The end 54 of vessel 50 may be turned outwardly, as shown in FIG. 3B, which exposes the intimal surface of the vessel. It will be understood that the end 54 of the vessel 50 could also be turned and everted over the collar 62, i.e., back toward the plate 64, rather than simply flared over the end of the collar 62, as shown in FIGS. 3B–3C.

Referring to FIG. 3C, the fastener 60 is moved toward the base 58 and the sharpened ends 80 of the prongs 78 pass through the tissue of vessel 50. Each prong end 80 then enters the space 74 between a pair of arms 72. The prong locking elements 82 lockingly engage the ends 73 of the arms 72 in ratchet-like fashion. The fastener 60 is moved farther toward the base 58 until the fastener base 76 presses the vessel end 54 against the end of the collar 62, and in particular against the ends of the middle and outer sleeves 66, 68. The prong locking elements 82 and the arm ends 73 maintain the base 58 and fastener 60 in the desired relative position vis-avis the vessel 50.

Figure 4A:
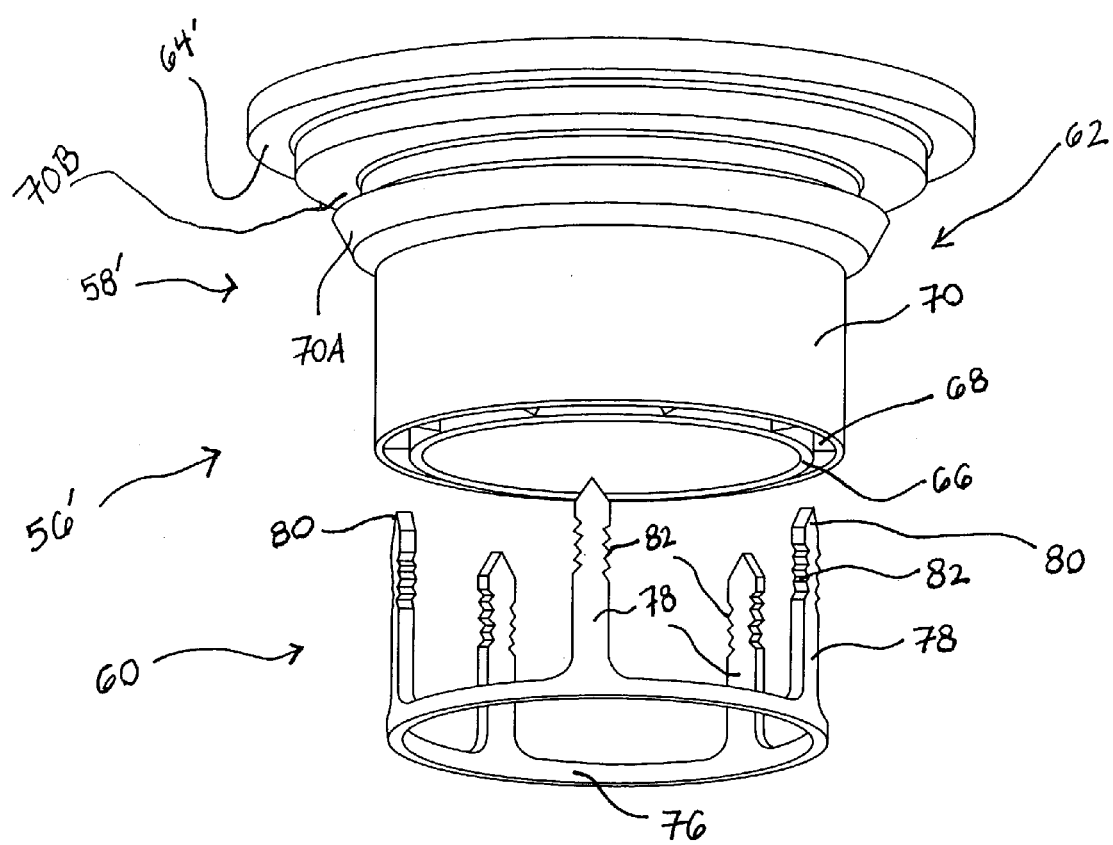
FIG. 4A is an exploded perspective view of the anastomotic component shown in FIGS. 3B and 3C.
Figure 4B:
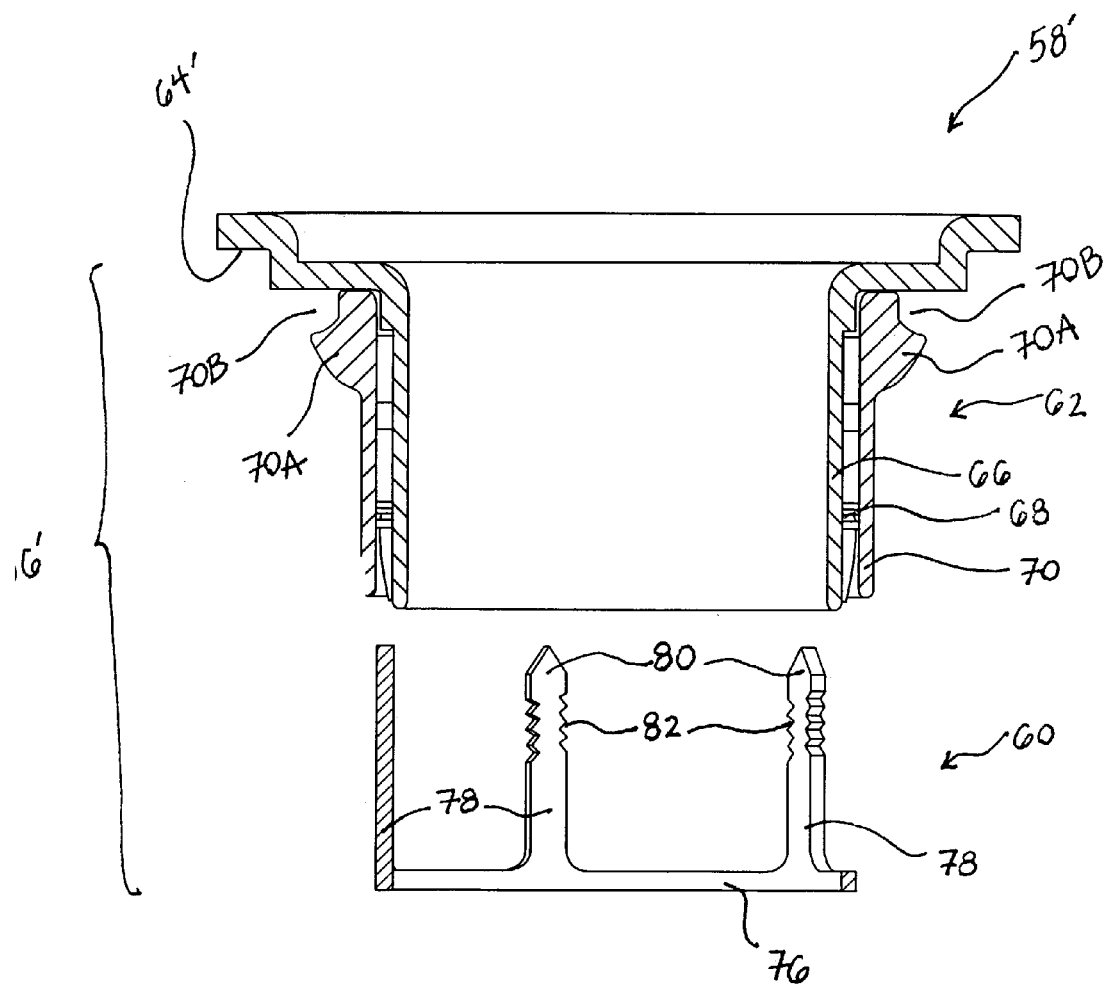
FIG. 4B is an elevation view, in section, of the anastomotic component shown in FIG. 4A.

FIGS. 4A–4B show the locking relationship between the fastener 60 and an anastomotic component that is designated by reference numeral 56' in view of structural differences from the anastomotic component 56 shown in FIGS. 3A–3C. In particular, the anastomotic component 56' of FIGS. 4A–4B is provided with a coupling mechanism (described below) that locks with a complementary mechanism on another component. It should be noted that the specific construction of either component may be varied from the exemplary configurations illustrated in the Figures.

FIGS. 4A–4B show the multiple sleeves of the collar 62 of the base 58'. In particular, FIG. 4B shows the sleeves 66, 68, 70 and how they cooperate to lockingly receive and engage the prongs 78 of fastener 60. The means for coupling the component 56 to another component are, in the illustrated embodiment, carried by the outer sleeve 70 and comprises a rim 70A extending around the collar 62. The rim 70A cooperates with the plate 64' (modified from the plate 64 of FIGS. 3A–3C) to form a recess 70B. This recess 70B is configured to engage a portion of another anastomotic component (not shown) in a snap-fit manner to create a fluid-tight anastomotic connection. These Figures show only one possible means for coupling the anastomotic component 56 to a second anastomotic component (not shown).

The anastomotic components of the embodiments of FIGS. 1A–2B and FIGS. 3A–4B are adapted to be secured to the end of a vessel and may be used to create various types of anastomoses (e.g., end-to-side or end-to-end). The present invention also encompasses anastomotic components that are designed to be secured to the side wall of a vessel (rather than its end). An exemplary embodiment of such a component will be described with respect to FIGS. 5–10.

Figure 5:
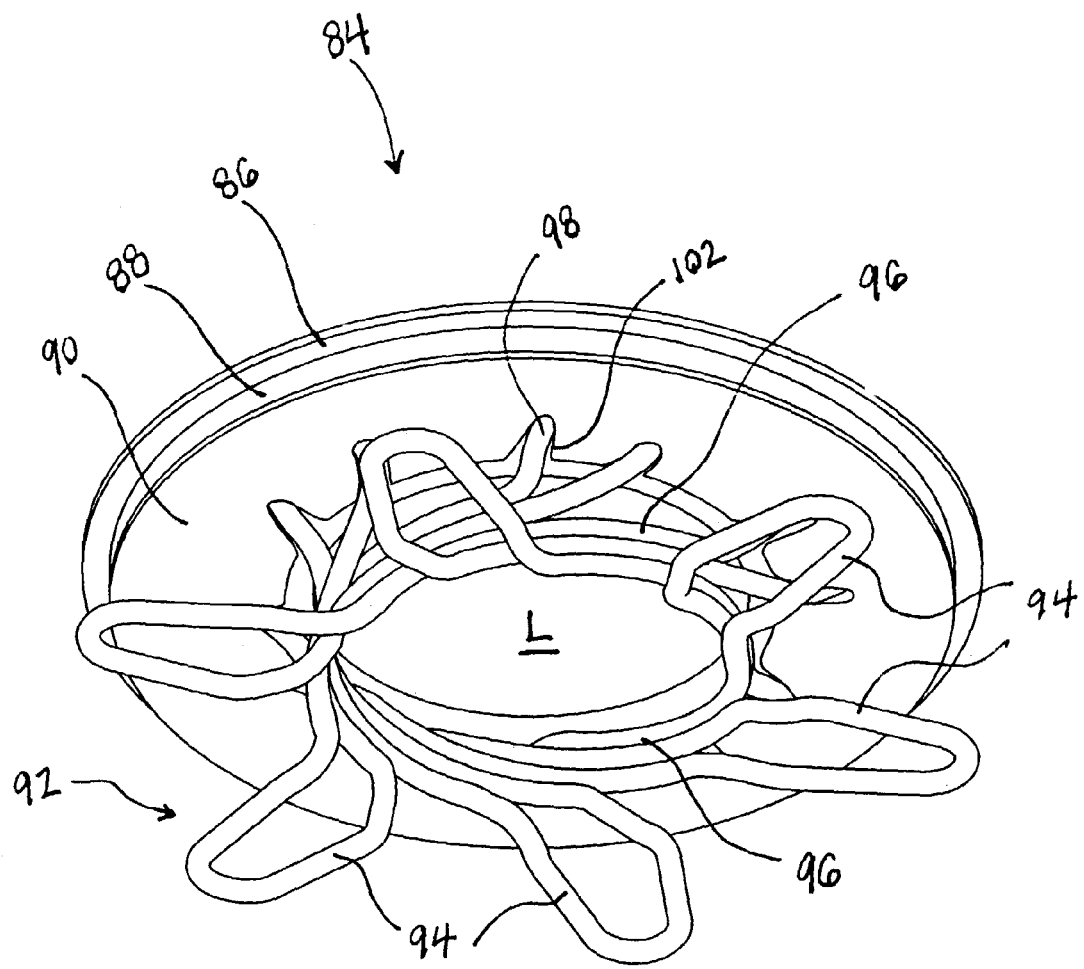
FIG. 5 is a lower plan view of an anastomotic component constructed according to another embodiment of the invention.
Figure 6:
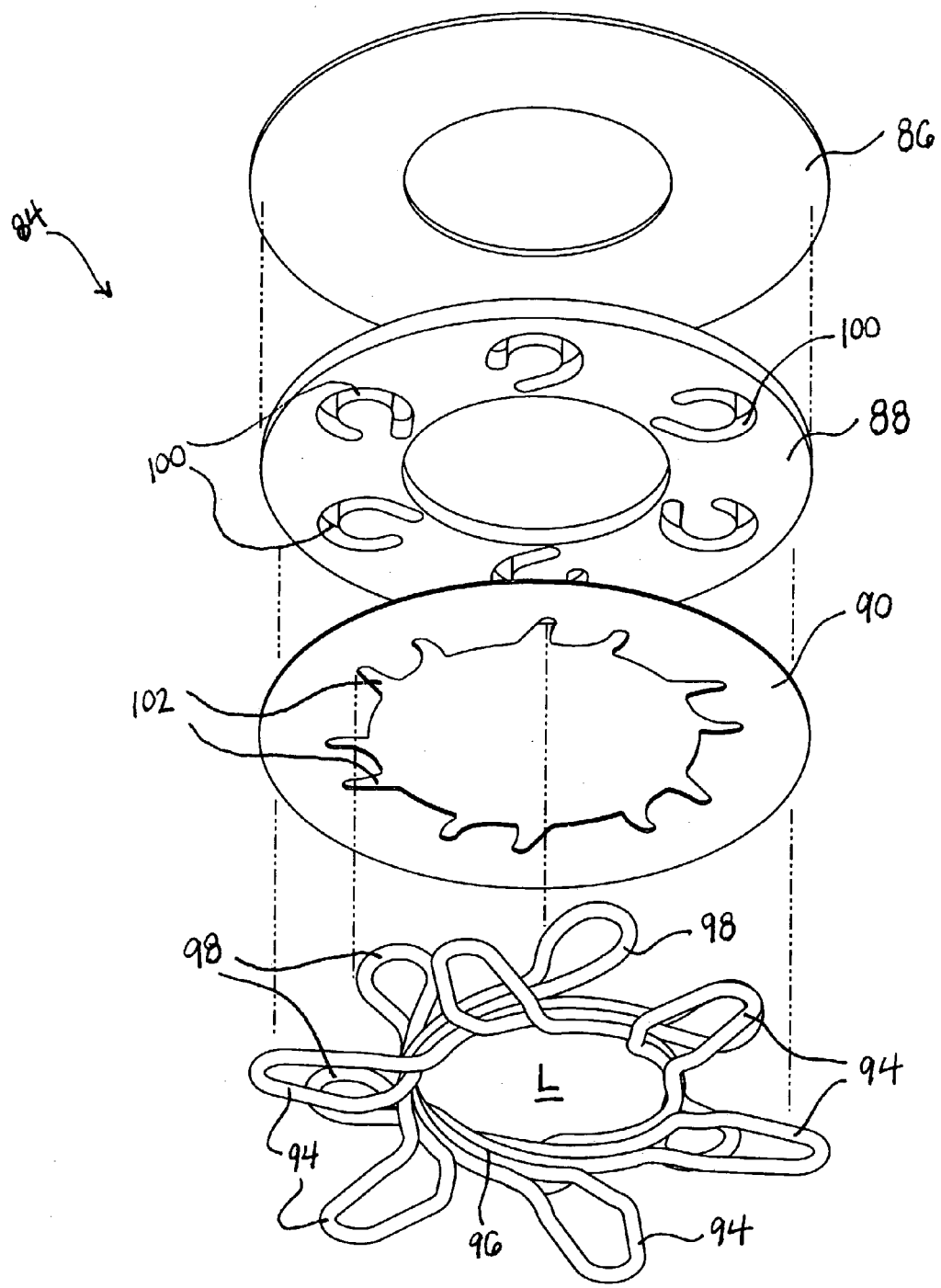
FIG. 6 is an exploded perspective view of the anastomotic component shown in FIG. 5.

FIG. 5 is an assembly view of an anastomotic component 84 which is configured to be secured to the sidewall of a vessel according to one embodiment of the invention. The anastomotic component 84 comprises a base 86, a body 88 and a retention plate 90. The component 84 is provided with a vessel attachment mechanism which, in the illustrated embodiment comprises a wireform coupling structure 92. The coupling structure 92 includes a plurality of vessel engagement members preferably in the form of a plurality of first wire loops 94. The first wire loops 94 extend from one end of a coil portion 96, which defines a lumen L passing through the component. A plurality of second wire loops 98 extend from the other end of the coil portion 96 (FIG. 6). The second set of wire loops 98 is used to secure the coil portion 96 and coupling structure 92 to the base 86 and body 88 of the anastomotic component 84.

Figure 11:
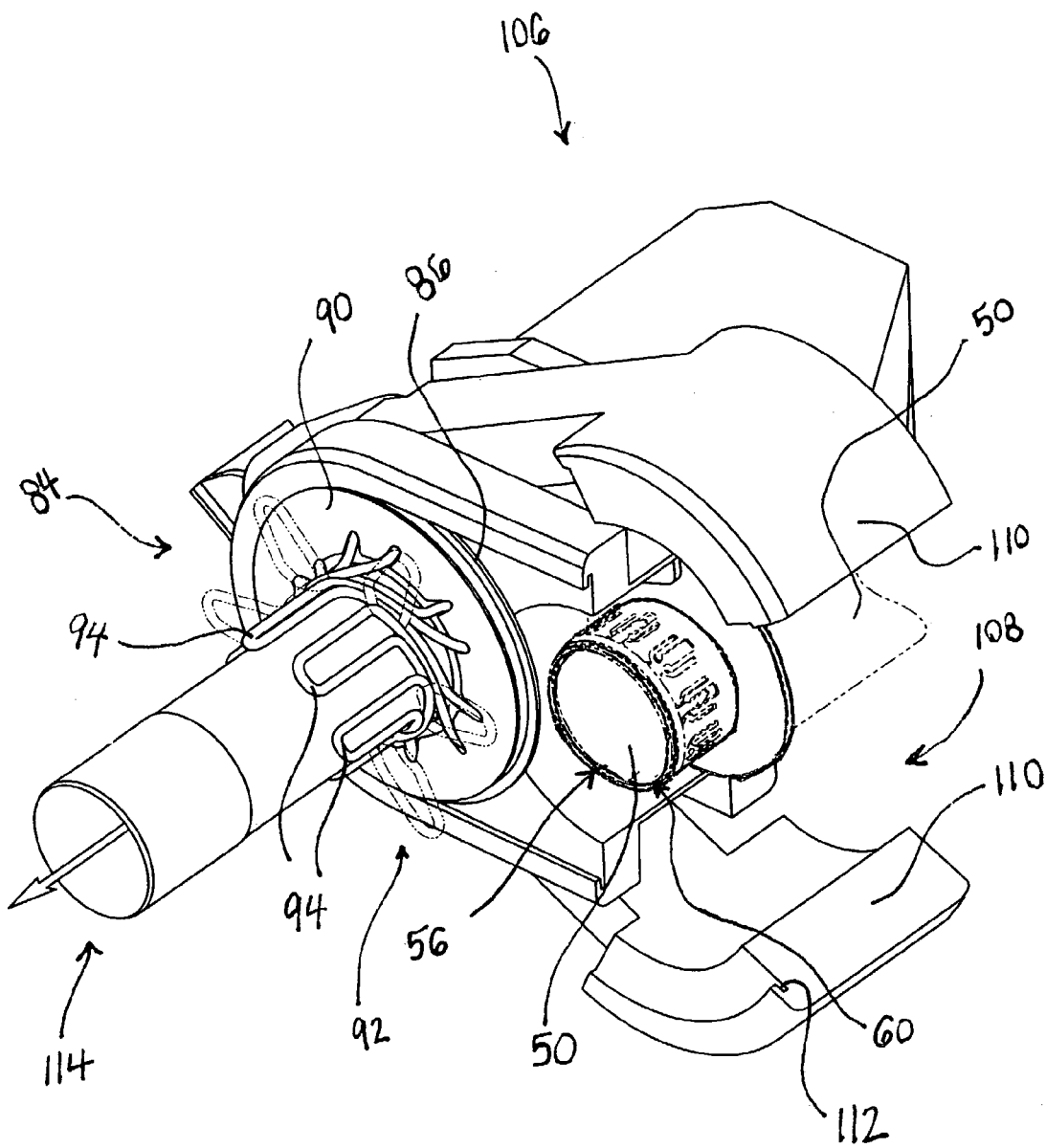
FIG. 11 is a perspective view of a delivery device constructed according to one embodiment of the invention, wherein the anastomotic components shown in FIGS. 1–10 are loaded on the device.

The coupling structure 92 is formed to permit the first, vessel-engaging loops 94 to selectively collapse and expand, as explained below. FIGS. 5–10 show the coupling structure 92 with the vessel engaging loops 94 in their expanded, unbiased orientation. FIG. 11 shows the coupling structure 92 with the vessel engaging loops 94 biased to their collapsed or low profile orientation. In the illustrated embodiment, the loops 94 assume an axial position that is generally parallel to the lumen L of the anastomotic component 84; however, it will be appreciated that the loops 94 could be collapsed in a different manner or to a different extent than shown in the figures.

FIG. 6 shows one preferred manner of constructing the anastomotic component 84. It will be recognized, of course, that the specific configuration shown and described herein is made for sake of example and for purposes of making a complete disclosure, and is not intended to limit the scope of the present invention as defined by the claims.

Figure 7:
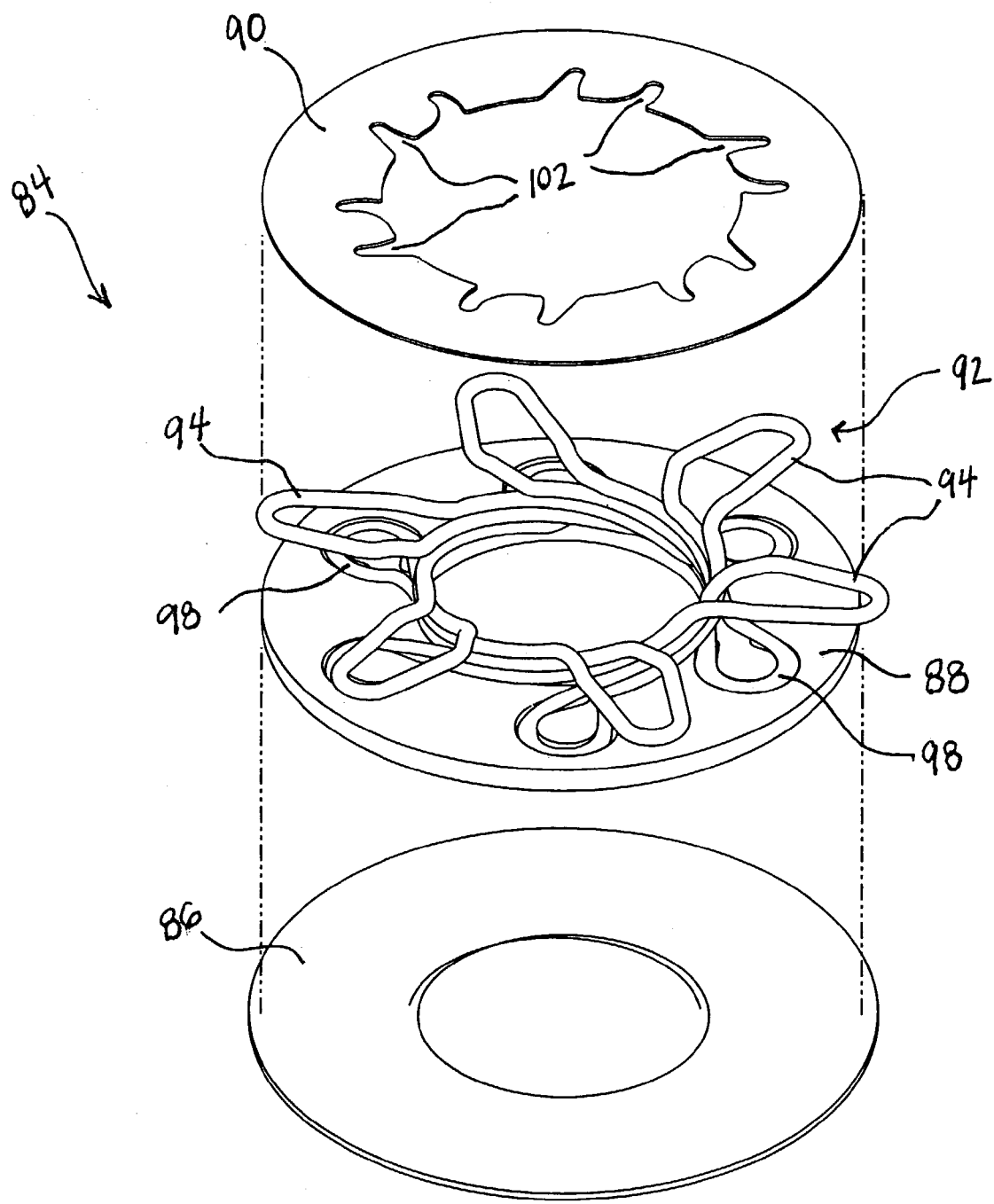
FIG. 7 is a perspective view of the anastomotic component shown in FIGS. 5 and 6 partially assembled.
Figure 8:
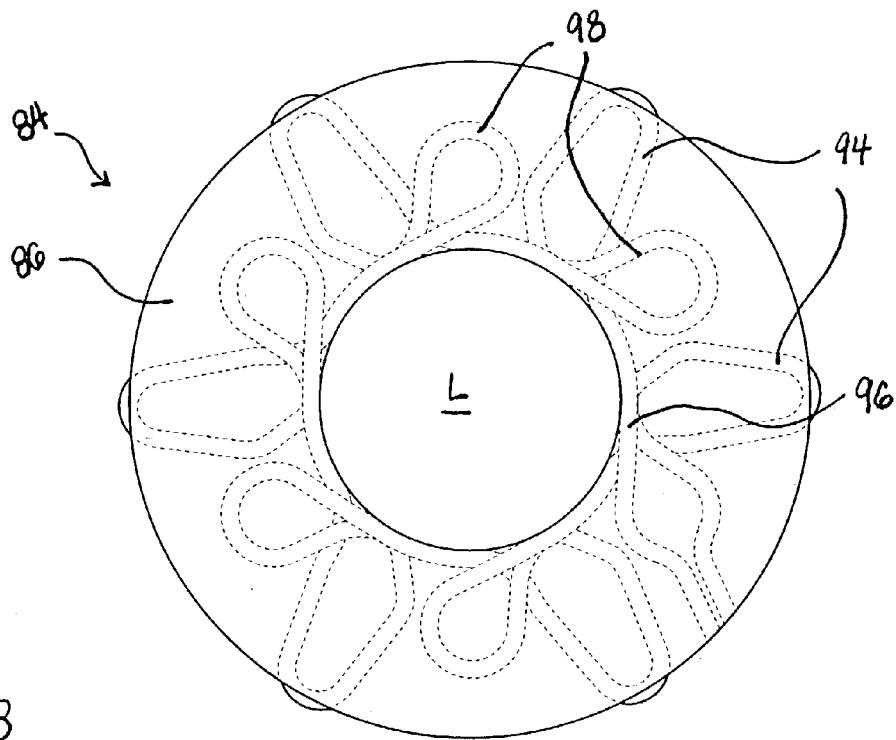
FIG. 8 is an upper plan view of the anastomotic component shown in FIG. 7.

Referring to FIG. 6, the base 86, body 88, retention plate 90 and coupling structure 92 of the anastomotic component 84 are annularly shaped so that when assembled they form a lumen L (FIG. 5) that extends through the component 84. The second set of wire loops 98 of the coupling structure 92 are positioned within complimentarily-shaped openings 100 formed in the body 88 (FIG. 7). The ends 104 of the coil that forms portion 96 and loops 94, 98 sit in corresponding grooves in the body 88. The body 88 is then attached to base 86, and the retention plate 90 is placed over the tissue-engaging loops 94, preferably while the loops 94 are biased to their collapsed orientation (FIG. 11).

Figure 9:
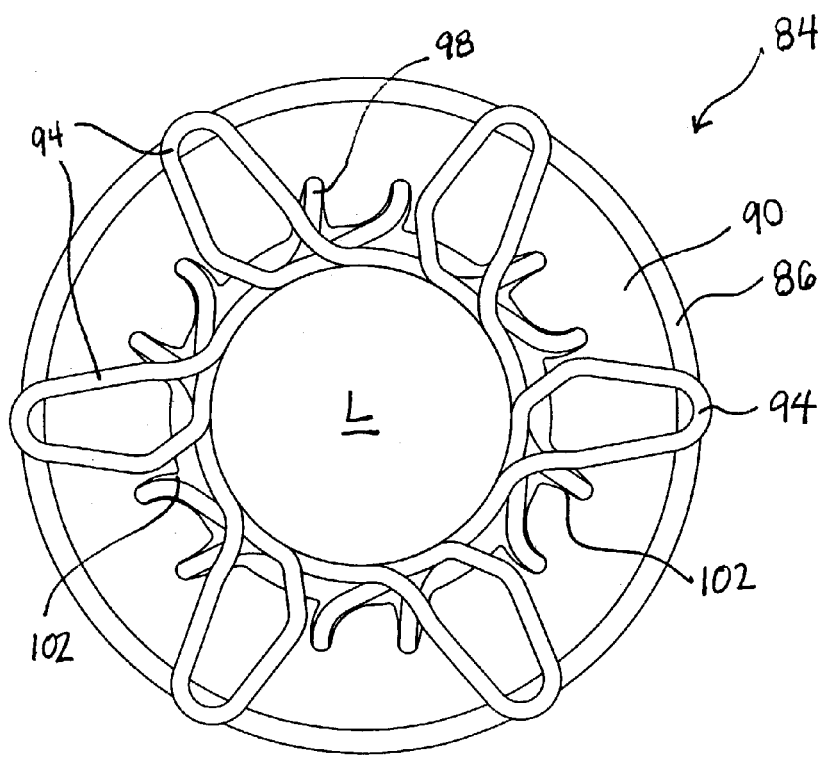
FIG. 9 is a lower plan view of the anastomotic component shown in FIG. 7.
Figure 10:
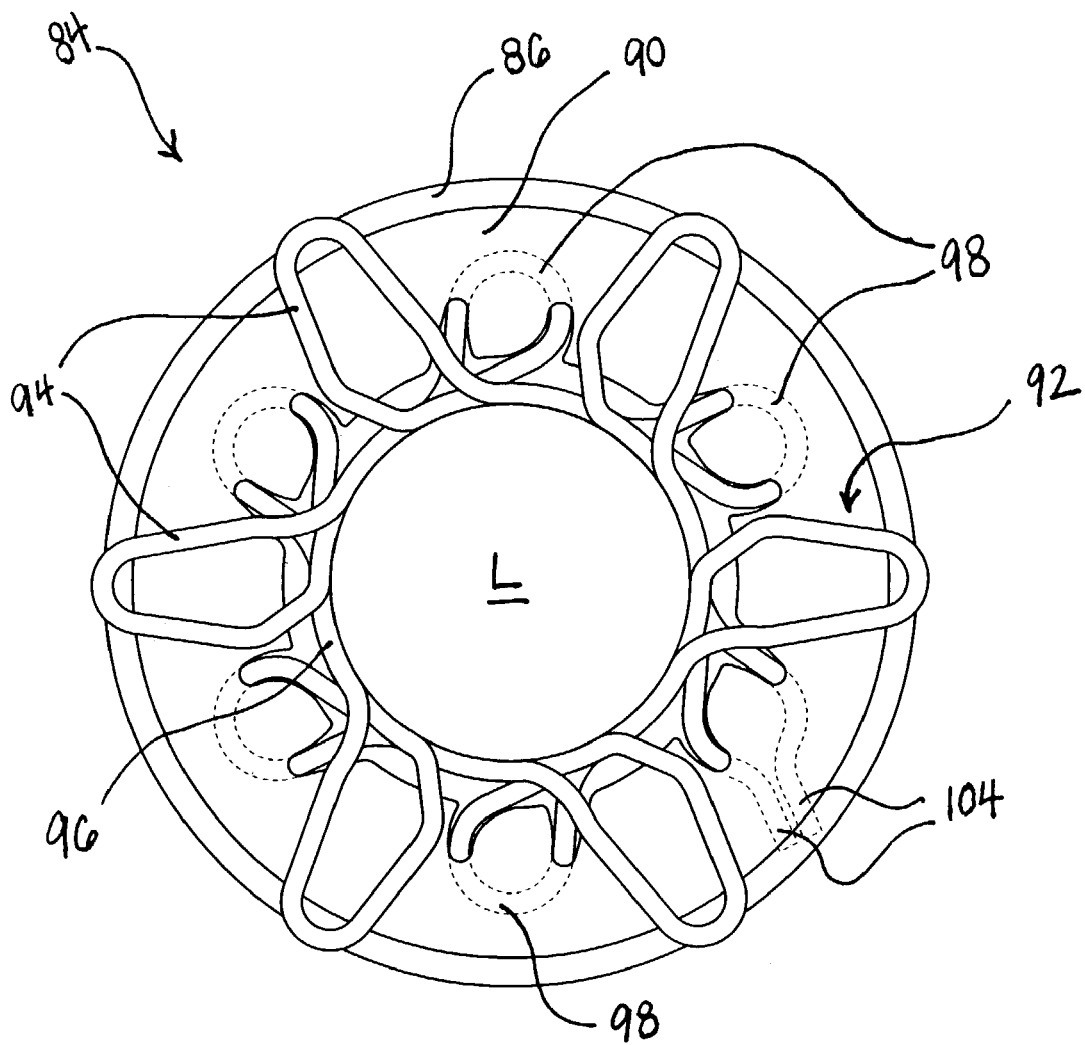
FIG. 10 is a lower plan view of the anastomotic component shown in FIG. 9 with securing portions of the component being indicated in phantom.

The retention plate 90 has a plurality of slots 102 (FIG. 6) that are positioned to overlie the openings 100 in the body 88. The slots 102 receive the legs of each loop 98 and position the loops 94 away from the retention plate 90, as shown best in FIGS. 5, 7 and 10. FIG. 9 shows the retention plate 90 secured to the remaining elements of the anastomotic component 84.

FIGS. 11–16 show the anastomotic component 56 of FIGS. 3A–4B after it has been secured to the end of the vessel 50 (shown in phantom). These Figures also show the anastomotic component 84 of FIGS. 5–10 prior to its attachment to the side wall of a vessel (not shown). The two components 56 and 84 are mounted in a delivery device 106 arranged to deploy one or both components to form the anastomosis. The exemplary embodiment connects two vessels via an end-to-side anastomosis; however, it should be appreciated that the invention may be used to make other types of connections, for example, end-to-end and side-to-side anastomoses.

The delivery device 106 includes a cradle 108 which receives the first anastomotic component 56 and the first vessel 50. The cradle 108 comprises a pair of jaws 110 movable between open (FIG. 11) and closed (FIG. 12) positions in order to mount the first anastomotic component 56 and vessel 50 in the delivery device 106. FIG. 11 shows the second anastomotic component 84 with the tissue engaging loops 94 of the coupling structure 92 collapsed for delivery, while FIG. 12 shows the coupling structure 92 expanded for engaging tissue (now shown)

Figure 12:
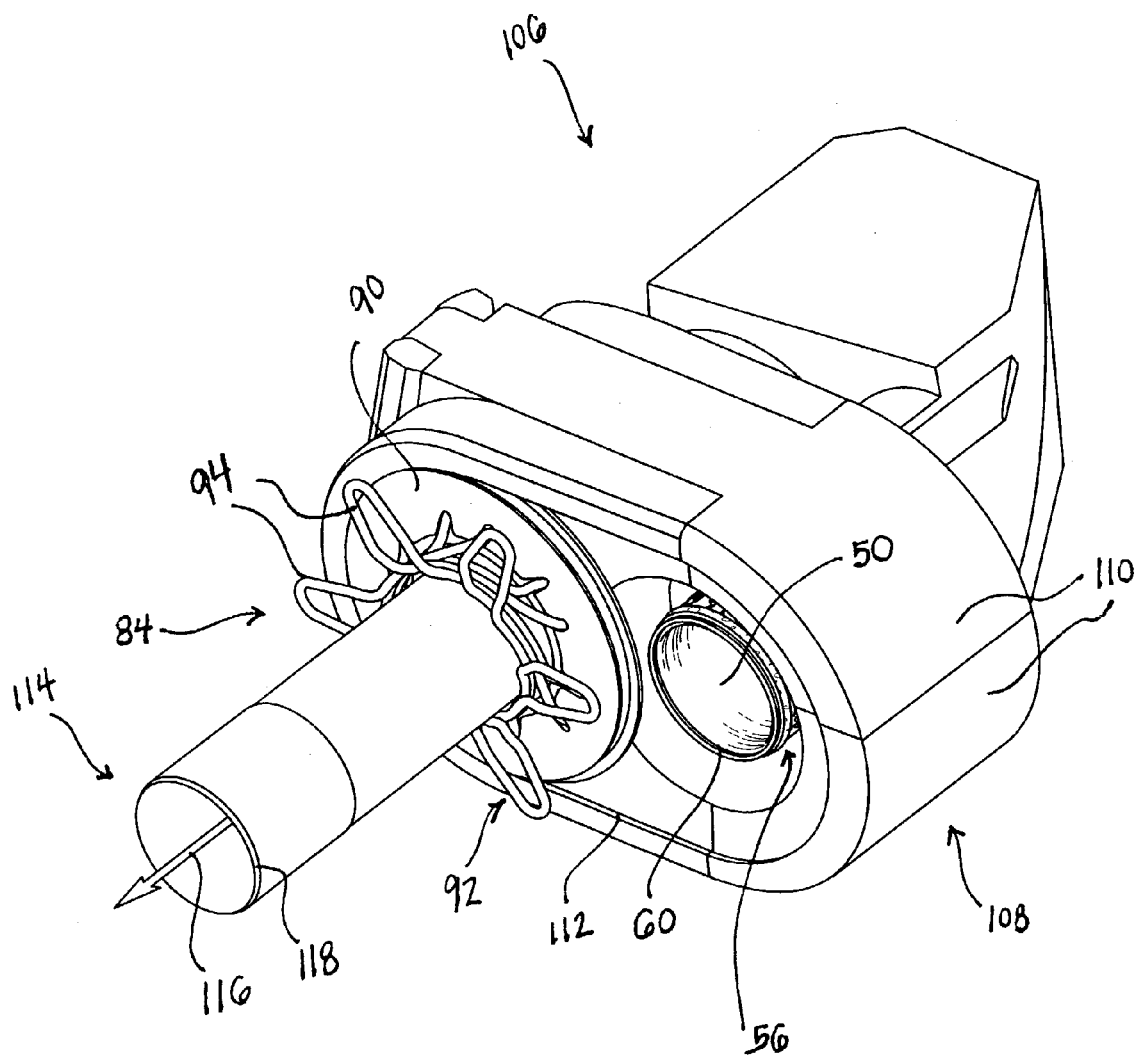
FIG. 12 is a perspective view showing the delivery device closed with the first and second anastomotic components locked in place, wherein the device includes a tissue removal mechanism.

As shown in FIGS. 11 and 12, the delivery device 106 may include a tissue removal mechanism 114 for forming an opening in a vessel that is placed in communication with the lumen L (FIG. 13) of the anastomotic component 84. The tissue removal mechanism 114 comprises a tissue holding element in the form of a barbed needle 116, and a tissue cutting tube 118 that is rotated in order to remove a desired amount of tissue. The tissue holding element is retractable in order to retract the needle 116 and pull the cut tissue into the tube 118 for removal. The means for moving the needle 116 and cutting tube 118 axially, and for rotating the tube 118, are not shown but may comprise any suitable drive or transmission assembly. The mechanism 114 is slidably disposed in a bore 120 in the delivery device 106 (FIG. 12).

Figure 13:
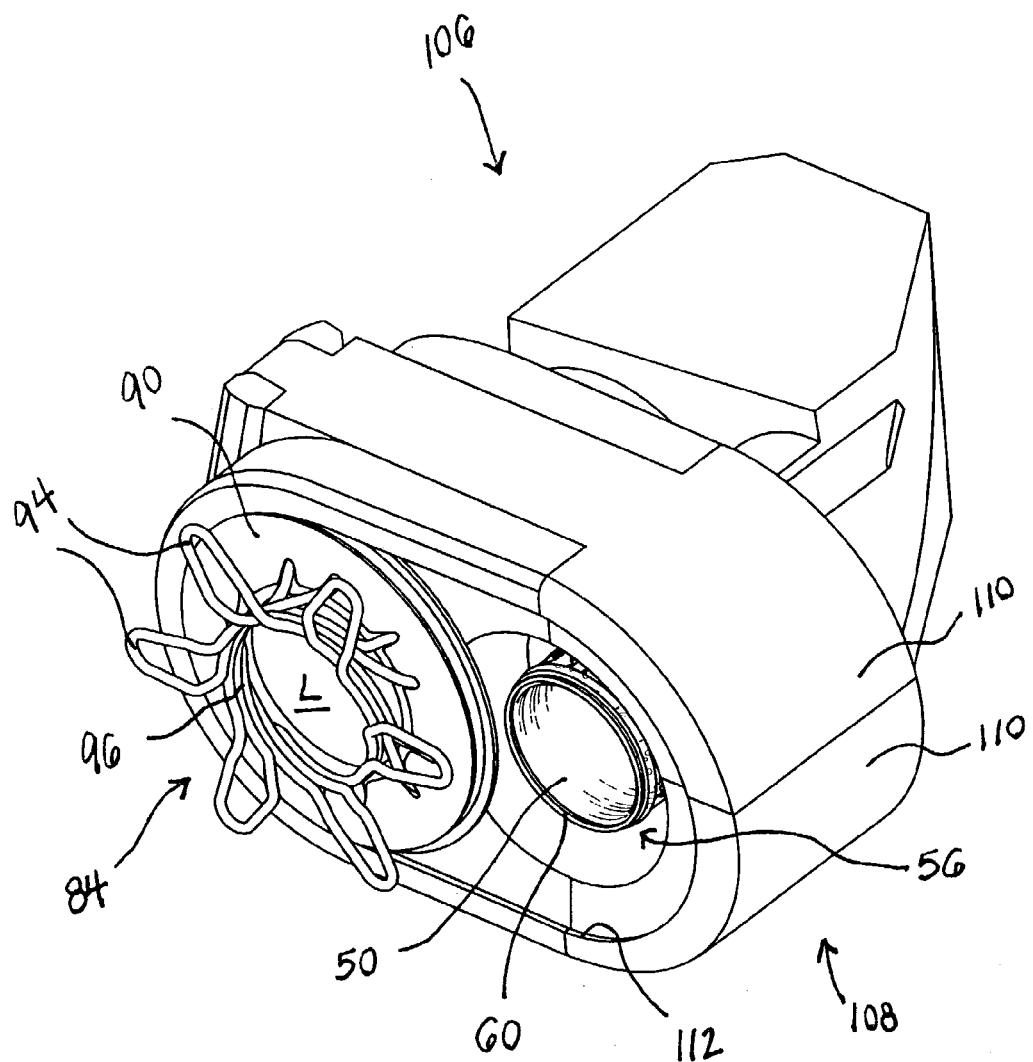
FIG. 13 is a perspective view of the delivery device shown in FIG. 12 after the tissue removal mechanism has been removed from the delivery device.

The tissue removal mechanism 114 is removed from device 106 (FIG. 13) after forming an opening in the vessel, and the second anastomotic component 84 is secured to the vessel (not shown) by expanding the helical loops 94. The second anastomotic component 84 is then aligned with the first component 56 by moving the device 106 and first component 56 relative to the second component 84 (and the second vessel). The two anastomotic components 56, 84 are initially unaligned, as shown in FIGS. 11–13. The delivery device 106 is moved from the position shown in FIG. 13 to the position shown in FIG. 14, which shifts the first anastomotic component 56 and first vessel 50 into alignment with the second anastomotic component 84.

The jaws 110 of the cradle 108 are provided with grooves 112 (FIG. 11) configured to receive the base 86 of the second anastomotic component 84 in a sliding manner. This facilitates controlled movement of the device 106 with respect to the second anastomotic component 84, from the position shown in FIG. 13 to the position shown in FIG. 14.

Figure 14:
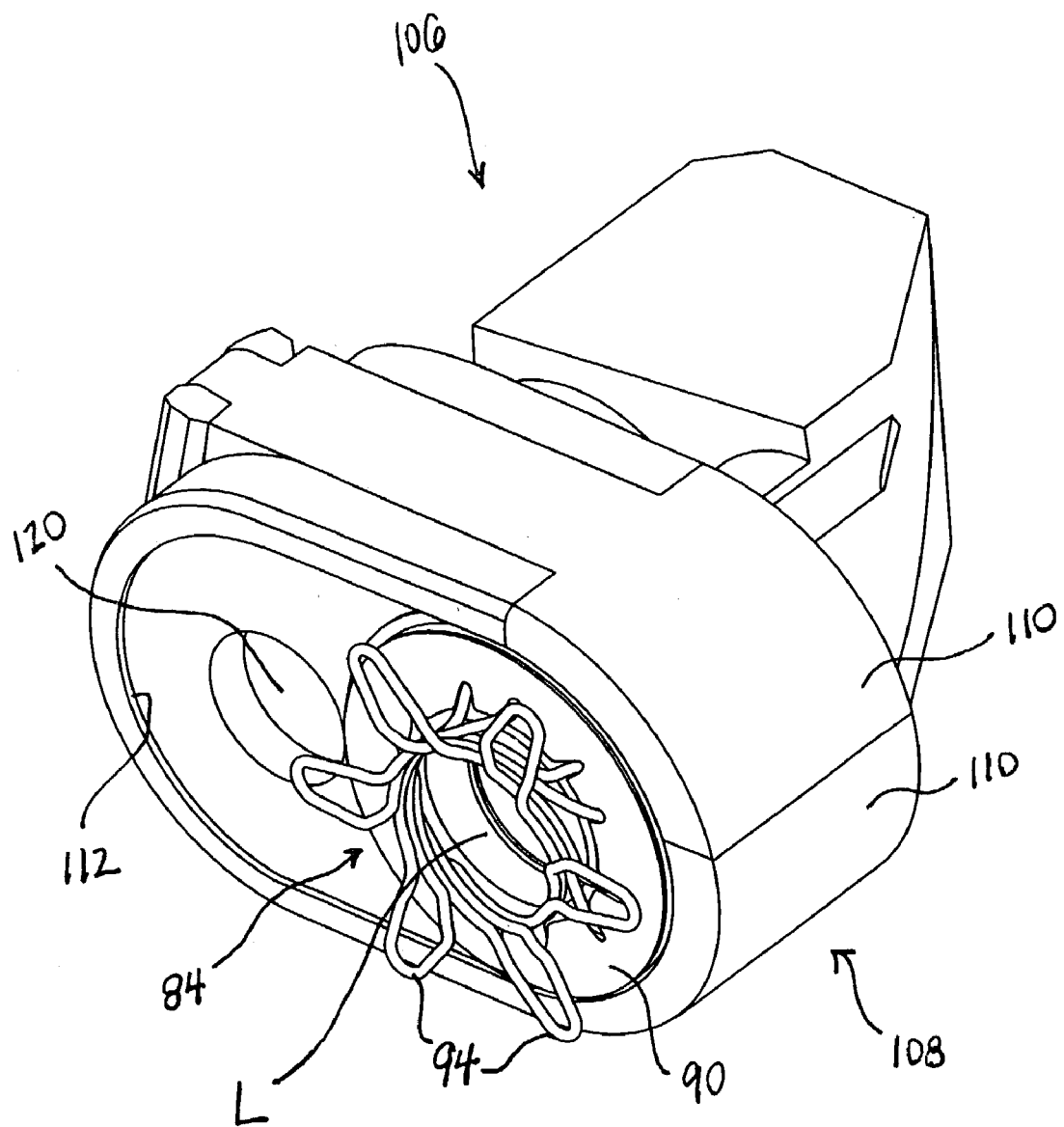
FIG. 14 is a perspective view showing the delivery device of FIG. 13 shifted relative to the second anastomotic component.
Figure 15:
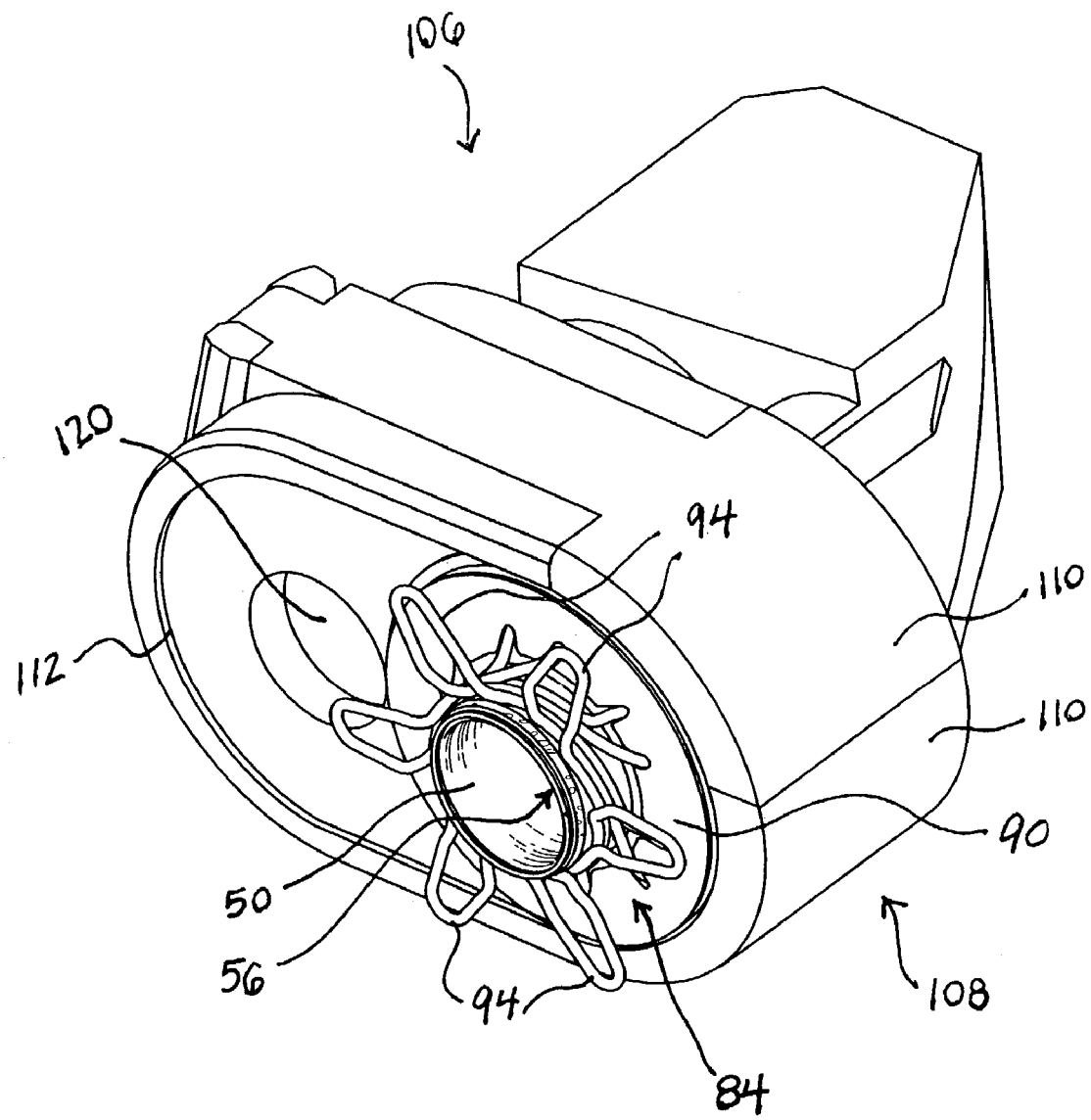
FIG. 15 is a perspective view showing the first anastomotic component moved into locking engagement with the second anastomotic component.

After being aligned, the first and second anastomotic components 56, 84 are secured to each other to place the lumens of the first and second vessels in communication and complete the anastomosis. In the illustrated embodiment, this is accomplished by moving the first anastomotic component 56 distally from the position shown in FIG. 14 to the position shown in FIG. 15, which moves component 56 into engagement with the second anastomotic component 84, as shown in FIG. 14. More specifically, the collar 62 of the first anastomotic component 56 is moved into the lumen L of the second anastomotic component 84 and enters the coil portion 96 of the wireform coupling structure 92. This moves the plate 64, 64' of the first anastomotic component 56, 56' next to, and preferably against, the exterior of the base 86 of the second anastomotic component 84.

FIG. 16 shows the delivery device 106 after the jaws 110 of cradle 108 have been opened to release the first and second anastomotic components 56, 84. The grooves 112 of the device 106 release the base 86 of the second anastomotic component 84, which has been secured to its vessel. The delivery device 106 is removed from coupled components 56, 84, leaving the two vessels in communication to complete the anastomosis.

The anastomotic components of the invention may be secured together by any suitable means which, as noted above, may use mechanical or magnetic force (or both) to achieve coupling. In the illustrated embodiment, the anastomotic components are secured to the vessels as they are secured to each other, namely, mechanically. In another embodiment, for instance, the first component is attached to its vessel mechanically but is coupled to the second component magnetically, for example, in accordance with any of the teachings in the aforementioned priority applications. An exemplary mechanism for securing the anastomotic components will now be described with respect to FIGS. 17–21.

Figure 17:
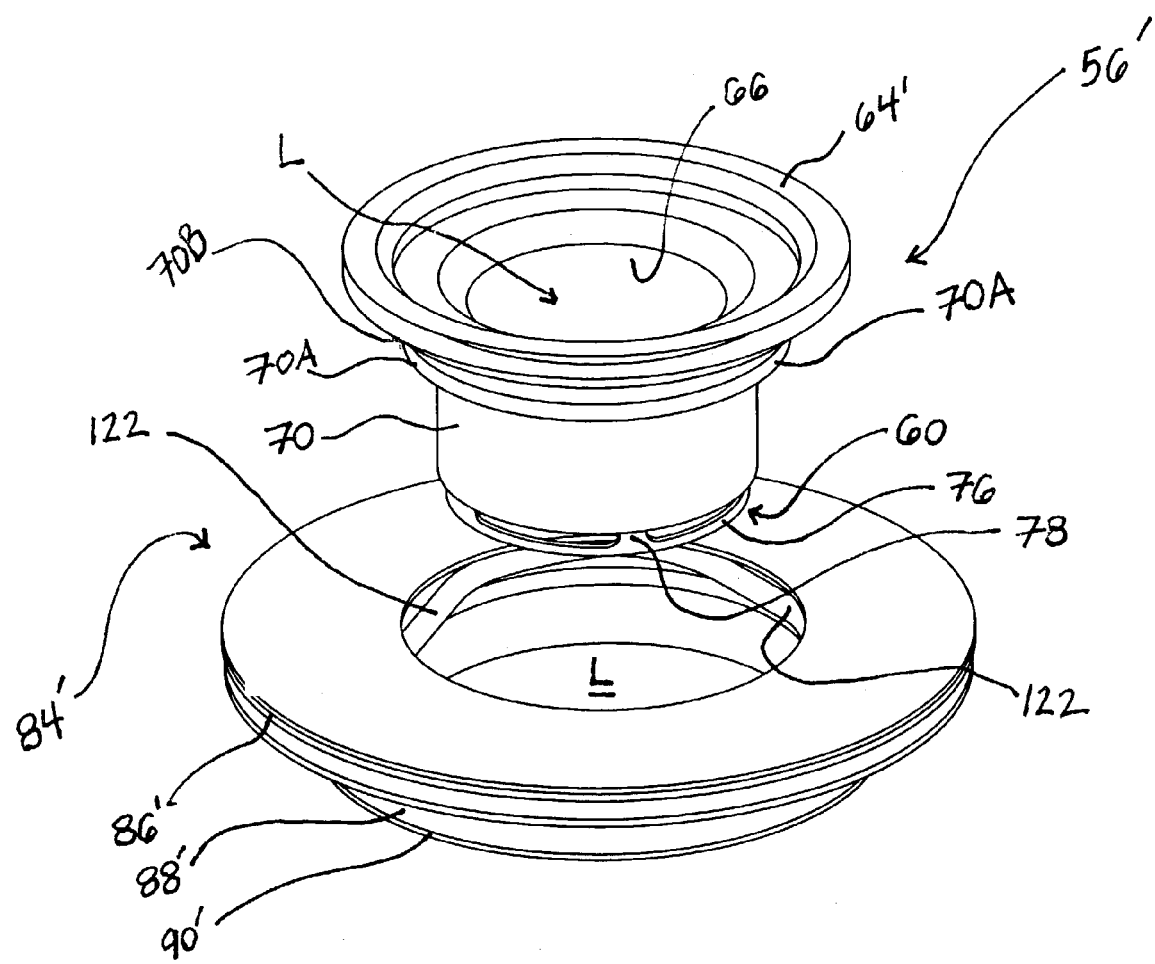
FIG. 17 is an exploded perspective view showing first and second anastomotic components constructed according to another embodiment of the invention.
Figure 18:
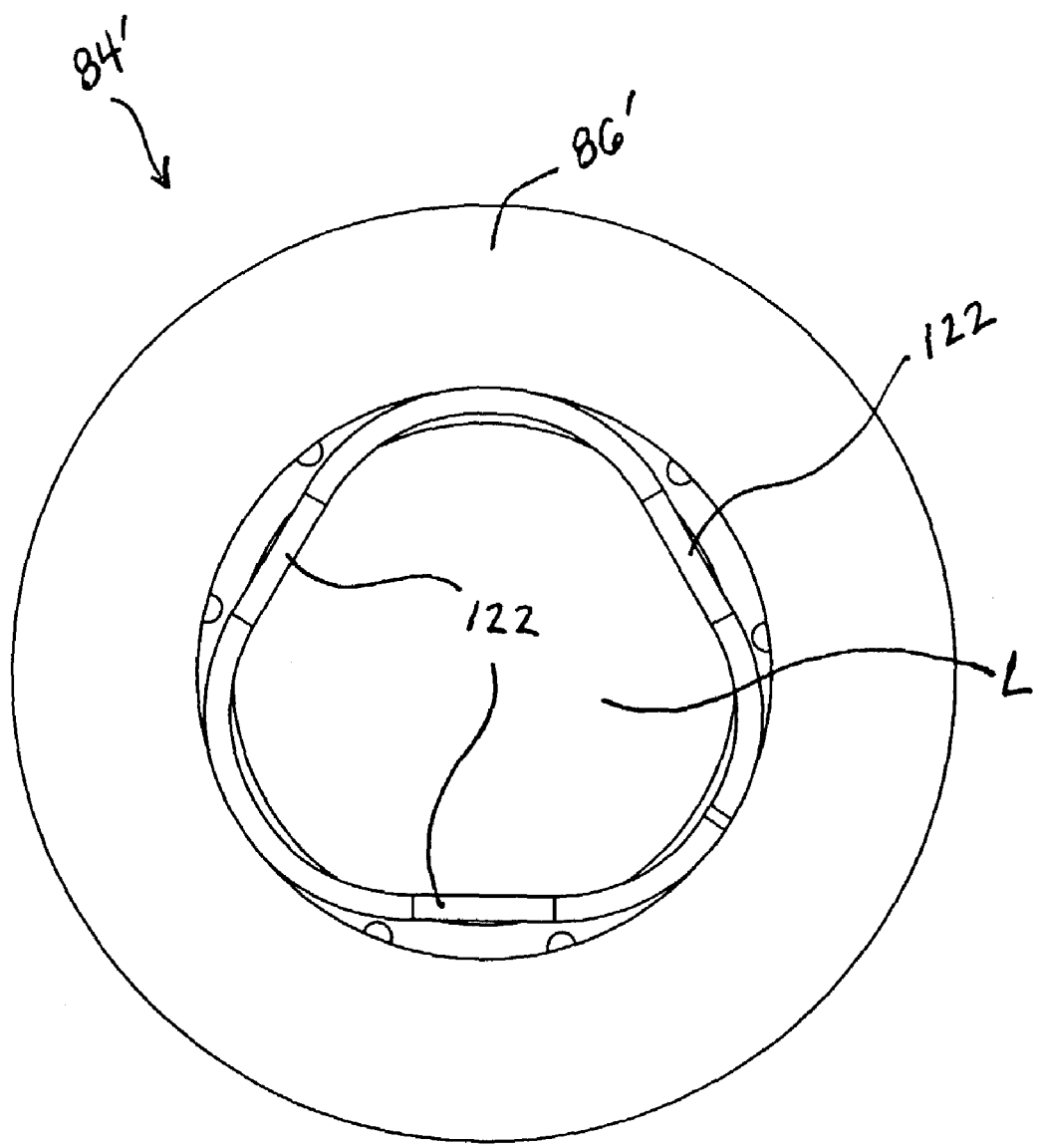
FIG. 18 is an upper plan view of the second anastomotic component shown in FIG. 17.
Figure 19:
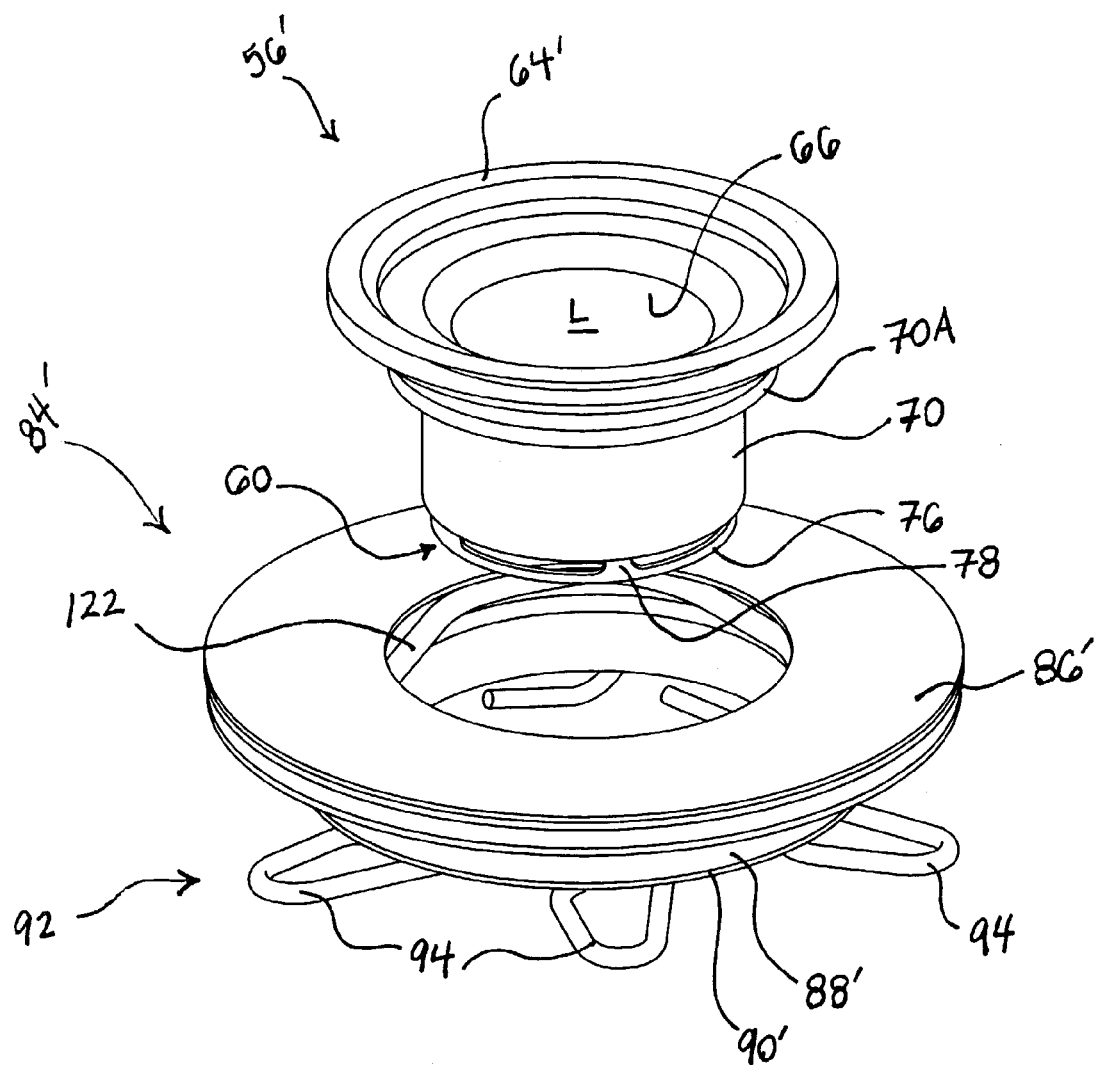
FIG. 19 is a perspective view corresponding to FIG. 17 wherein the second anastomotic component has been actuated to its tissue securing position.

FIG. 17 shows the first anastomotic component 56', which includes the modified plate 64' and rim 70 that define the recess 70B. The construction of the anastomotic component 56' is described above with respect to FIGS. 4A and 4B. The second anastomotic component is designated by reference numeral 84' as it, unlike the component 84, includes a mechanism for coupling the components. The illustrated mechanism is in the form of spring wires 122 which are located around the lumen L of the component 84'. See FIG. 18. FIG. 19 shows the first and second components 56', 84' of FIG. 17 after the component 84' has been deployed and the wire loops 94 are in their expanded orientation.

Figure 20:
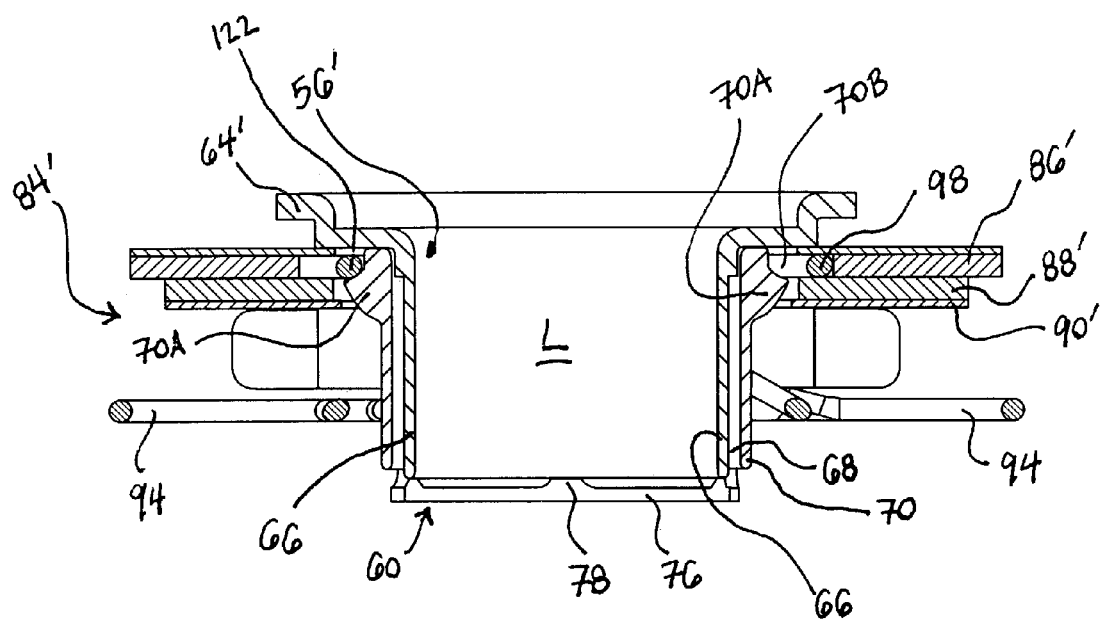
FIG. 20 is a sectional view showing the first and second components of FIG. 19 coupled.

FIG. 20 shows the first and second anastomotic components 56', 84' after they have been coupled, which, in this example, is done mechanically. As can be seen the spring wires 122 are received within the recesses 70B, preferably in tight locking fashion, for example, via a spring or snap fit engagement. Other possible locking mechanisms may of course be used.

Figure 21:
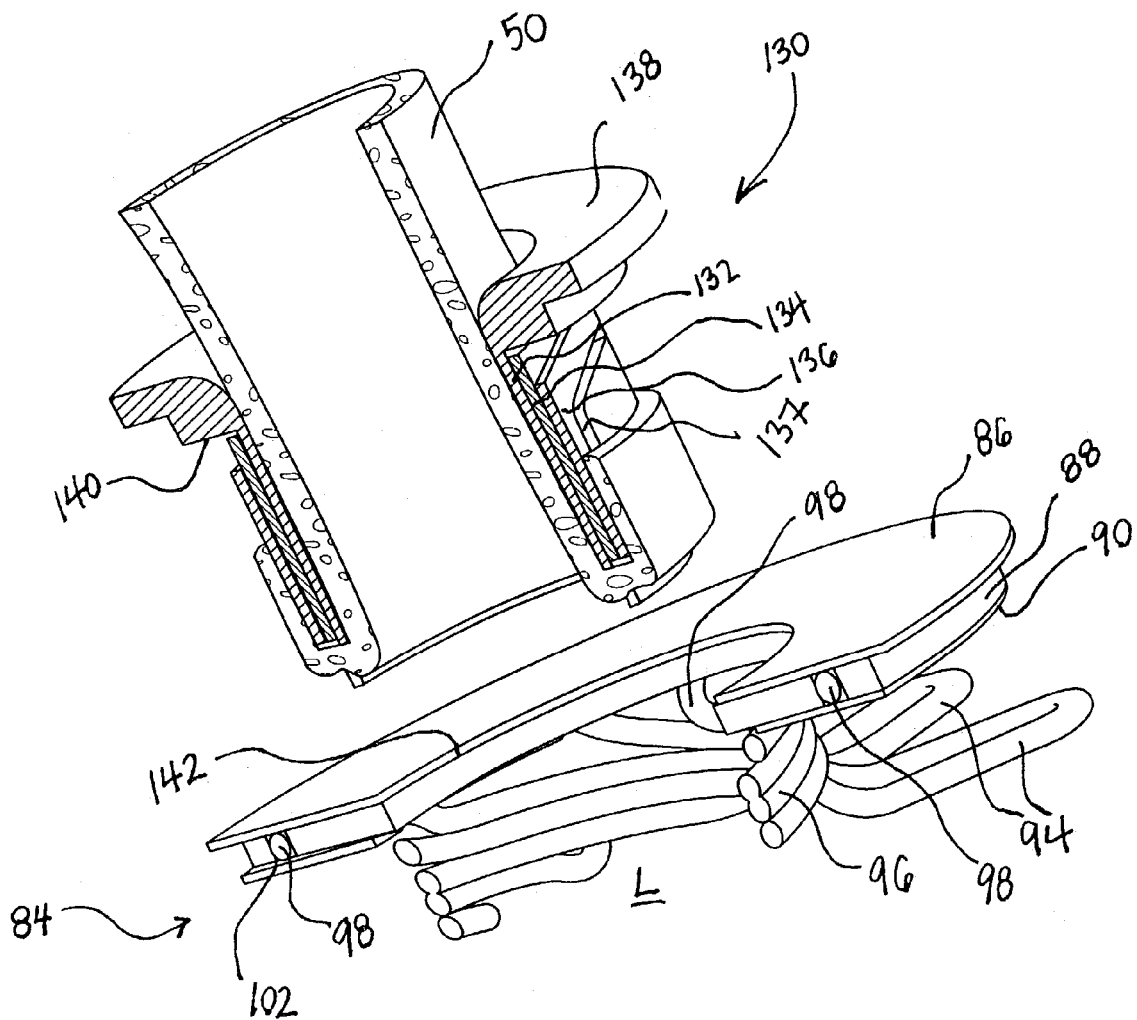
FIG. 21 is an exploded perspective view, in section, of the two components shown in FIG. 18 modified according to another embodiment of the invention.

FIG. 21 shows one alternative coupling mechanism or structure carried by a first anastomotic component 130. Specifically, the component 130 includes a multilayer collar comprising an inner layer 132, a middle layer 134 and an outer layer 136. The inner layer 132 is carried by a plate 138, and surface 140 is configured to rest on the plate 86 of the component 84. The outer layer 136 has one or more slots or grooves 137 configured to lockingly engage structure carried by the second anastomotic component 84. The second anastomotic component 84 includes plate 86 with an edge 142 (FIG. 21) that is received in some or all of the slot(s) 137 in the outer layer 136 of the first anastomotic component 130. It will be appreciated that the exact manner that the plate 86 engages the slot(s) 137 may vary widely while still providing a secure, sealed connection.

Figure 22:
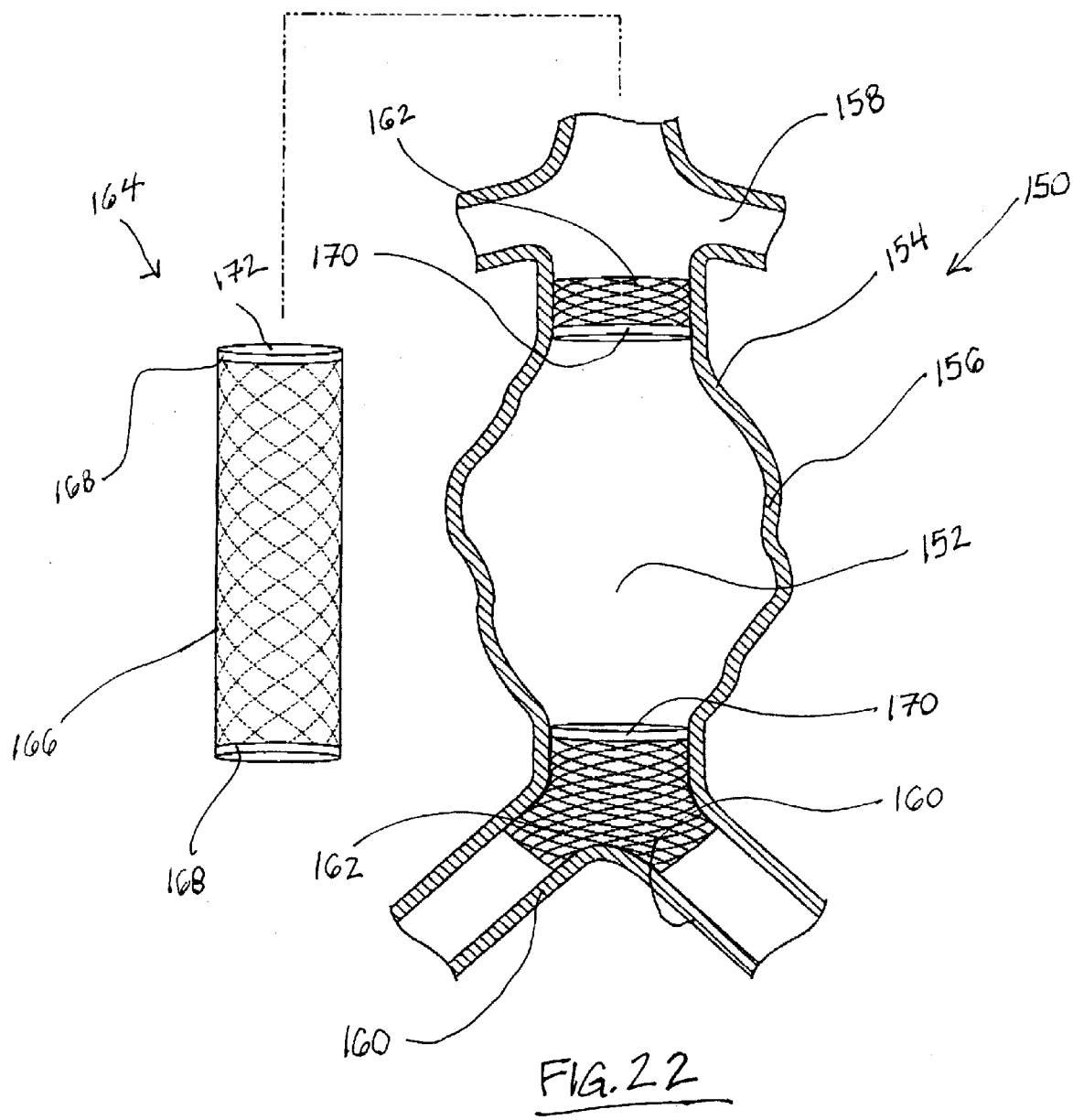
FIGS. 22, 23A and 23B are sequential perspective views, partially in section, showing a device constructed according to another embodiment of the invention being used to treat a diseased lumen in a patient's body.

Additional aspects of the invention will be described with respect to FIG. 22 through FIG. 29B, which show various systems, devices and methods for treating body lumens, i.e., hollow anatomical structures having a lumen, for example, a blood vessel. FIG. 22 shows a body structure in the form of a blood vessel, and more specifically, the abdominal aorta. The vessel is designated generally by the reference numeral 150 and includes a lumen 152 defined by a wall 154. The wall 154 has an aneurysm 156 where the lumen 152 is enlarged and the wall 154 is thinner (although not in the Figures). The vessel 150 has side branches 158 and a Y-shaped section 160.

FIG. 22 also shows a pair of docking devices 162 secured to the wall 154 of the vessel 150, the devices being in the form of mesh structures expanded against the surface of the vessel wall 154. Also shown is a device 164 preferably in the form of a stent graft with a body 166 and attachment members 168 configured to engage attachment members 170 provided on the docking devices 162.

Figure 23A:
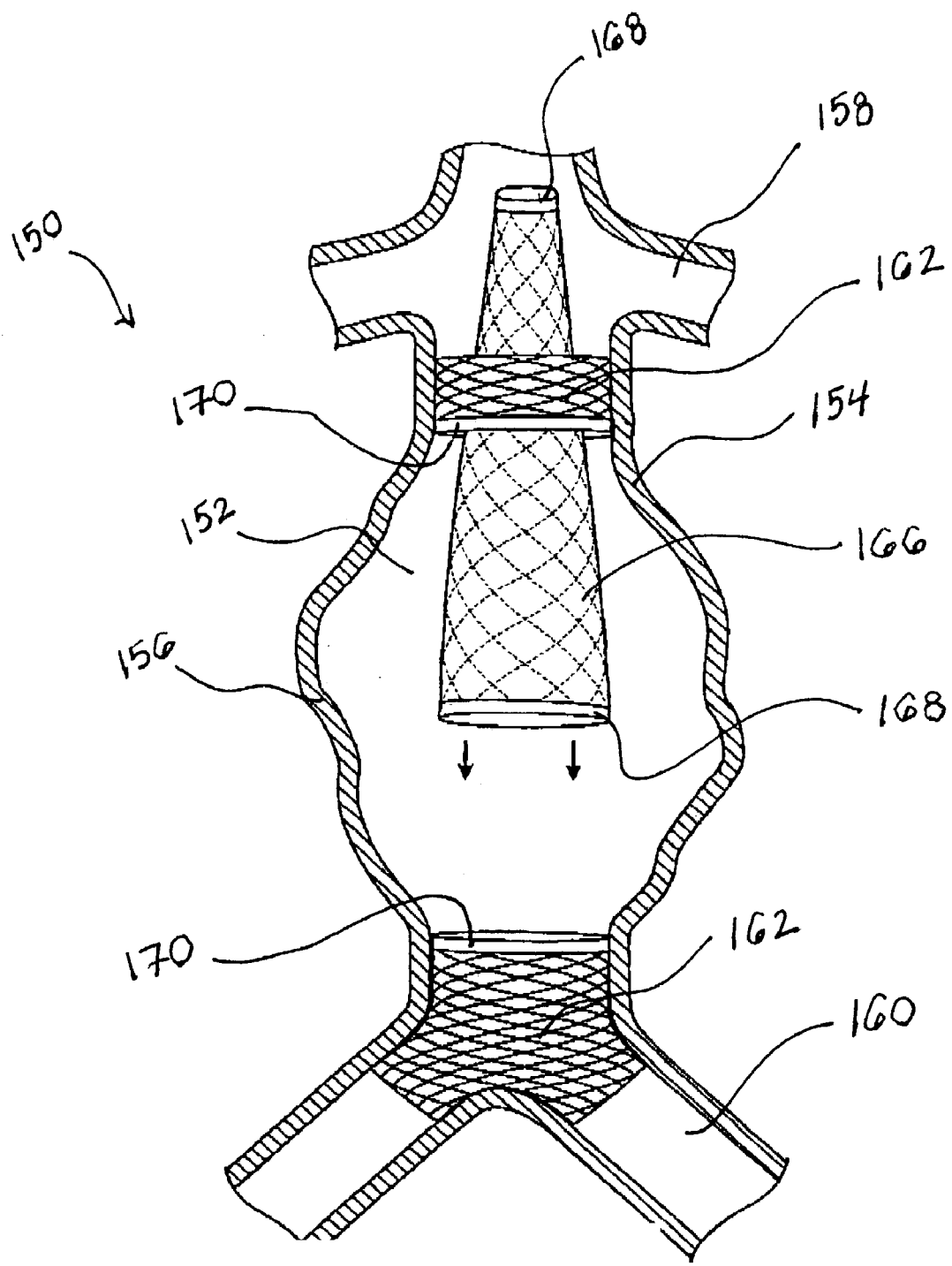
Figure 23B:
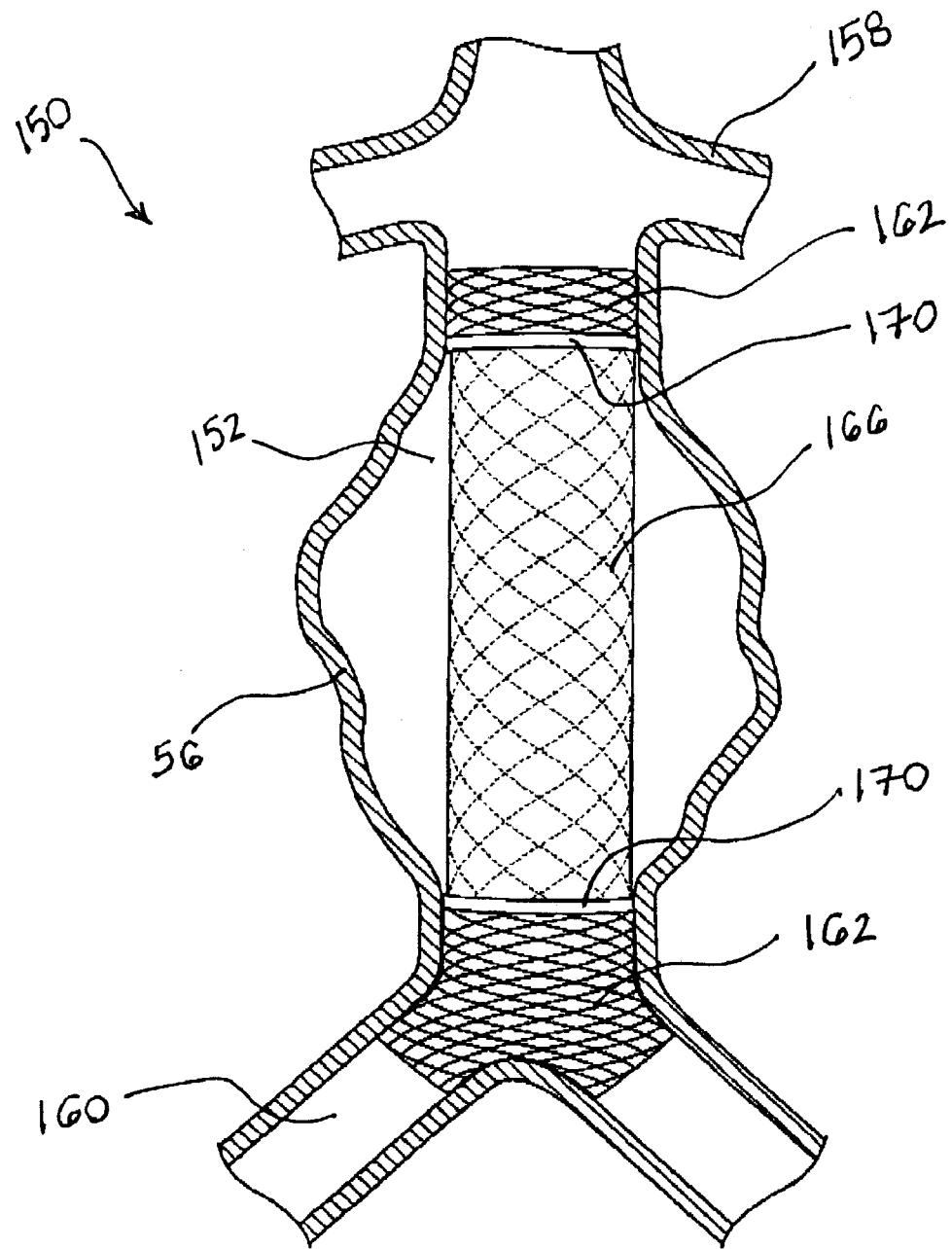

FIGS. 23A and 23B show the stent graft 166 being collapsed for delivery into the lumen 152 of the vessel 150. After being passed into the lumen 152 the graft body 166 is expanded and the attachment members 168 are coupled to the attachment members 170 of the docking devices 162. In the illustrated embodiment, the attachment members 168 and the members 170 are magnetically attracted so that upon being moved into proximity to each other they become securely connected. As a result, as shown in FIG. 23B, the device 164 extends through the aneurysmal section of the vessel 150 so that its lumen 172 replaces the diseased lumen. The docking devices 162 are in sealing contact with the vessel wall 154 and the stent graft 166 is in sealing contact with the docking devices. As such, blood flow past the aneurysm must take place through lumen 172 of the prosthesis.

Figure 24A:
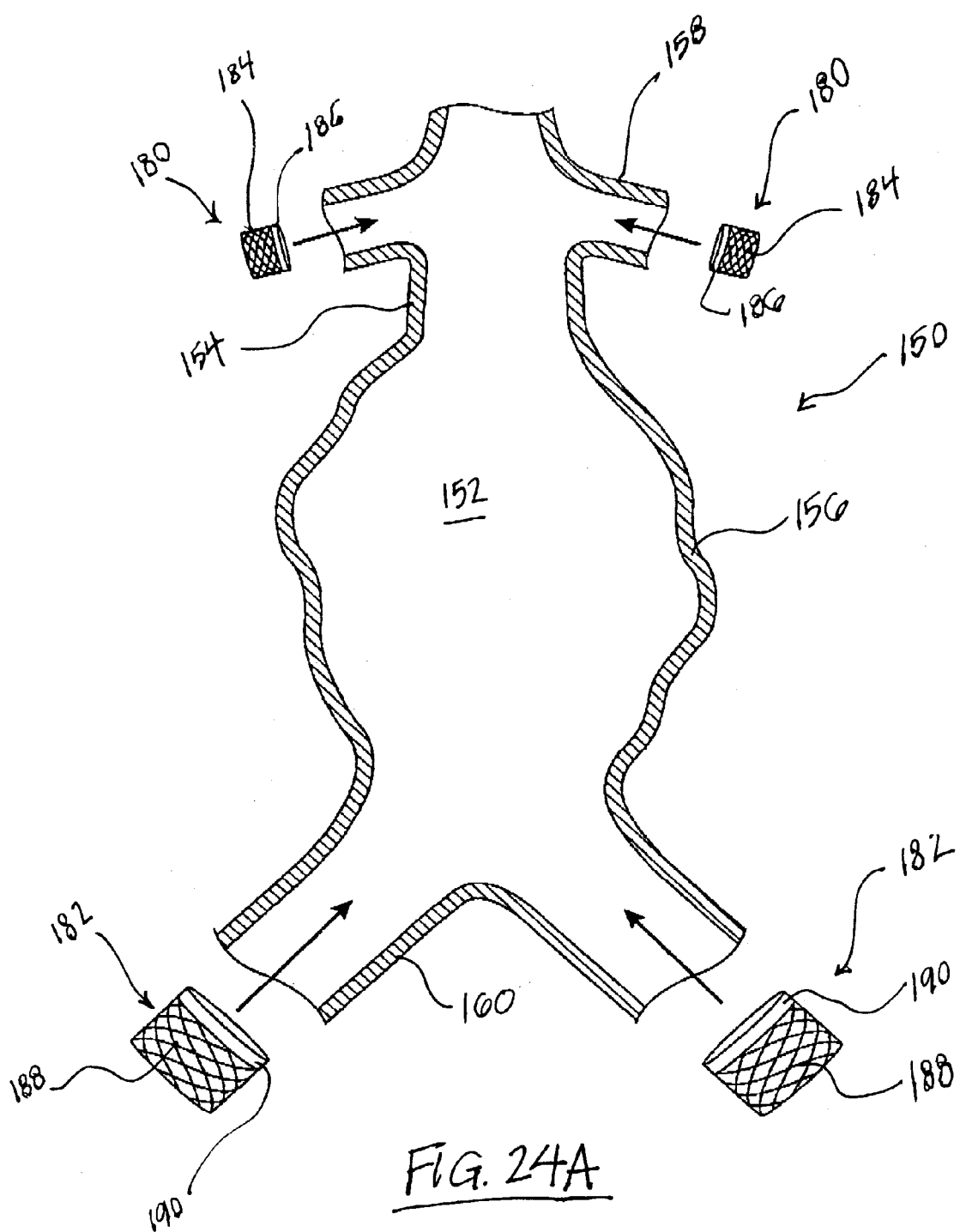
FIGS. 24A and 24B are sequential perspective views, in section, showing a device constructed according to another embodiment of the invention being used to repair a body lumen.
Figure 24B:
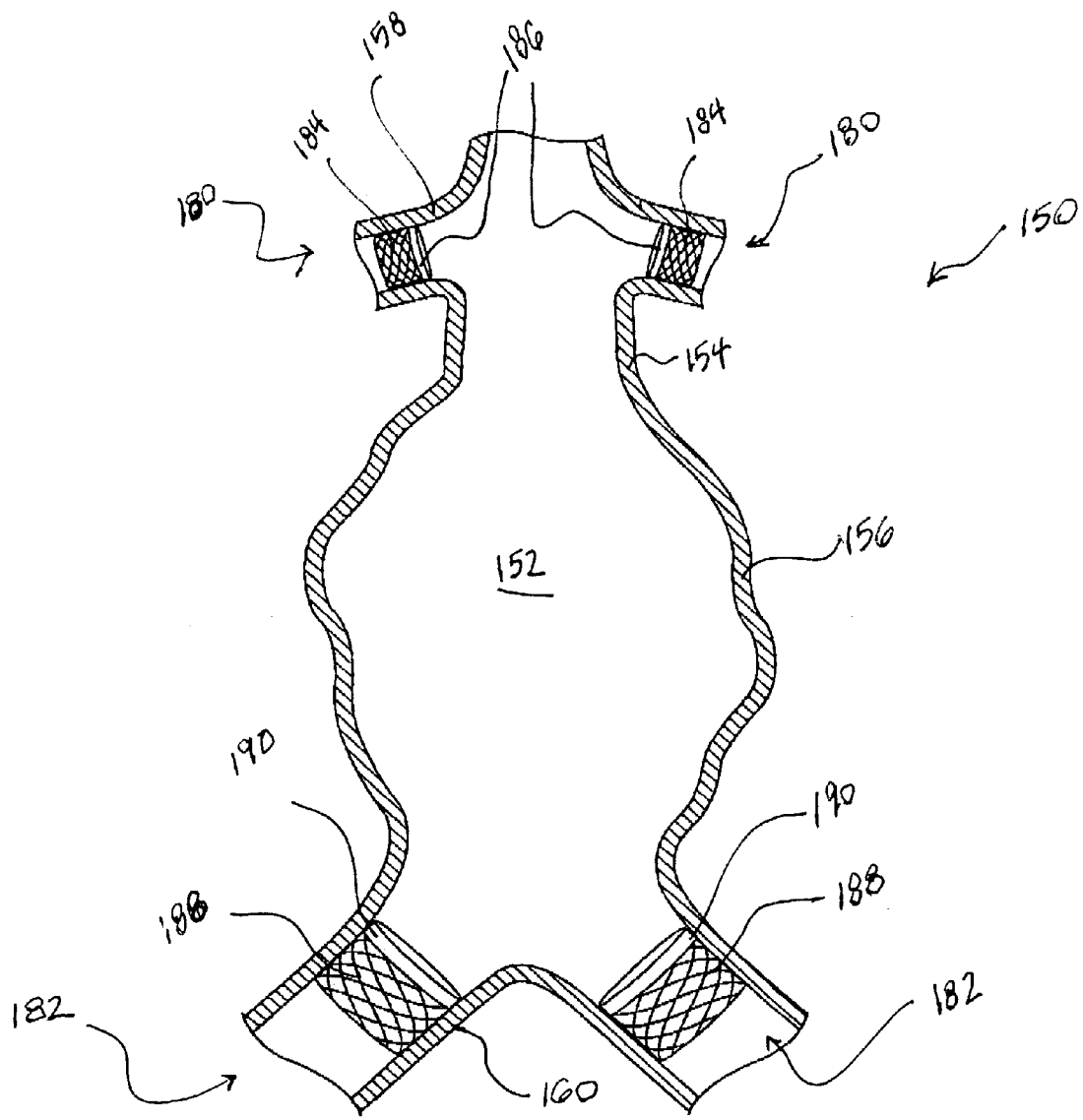

FIGS. 24A and 24B show another embodiment of the invention comprising a pair of proximal docking members 180 and a pair of distal docking members 182. The docking members 180 and 182 are shown in conjunction with the vessel 150 of FIG. 22 and FIGS. 23A–23B and may be constructed in any suitable manner that facilitates their attachment to a vessel wall, for instance, expansion against the vessel wall as described above with respect to the docking members 162 of the previous embodiment.

The proximal docking members each have a stent-like body 184 and an attachment portion 186, while the distal members each have a stent-like body 188 with an attachment portion 190. FIG. 24B shows the four docking members 180, 182 with members 180 secured to side branches 158 and members 182 secured to the Y-shaped section 160 of the vessel 150. The number and position of docking members used may vary upon application or user preference. Two different, exemplary approaches are shown in FIGS. 23B and 24B. Once the docking members 180 and 182 have been attached to the vessel wall in a secure sealed fashion as shown in FIG. 24B, a vascular prosthesis (not shown) is secured to the respective attachment portions 186, 190 of the members 180 and 182.

Figure 25A:
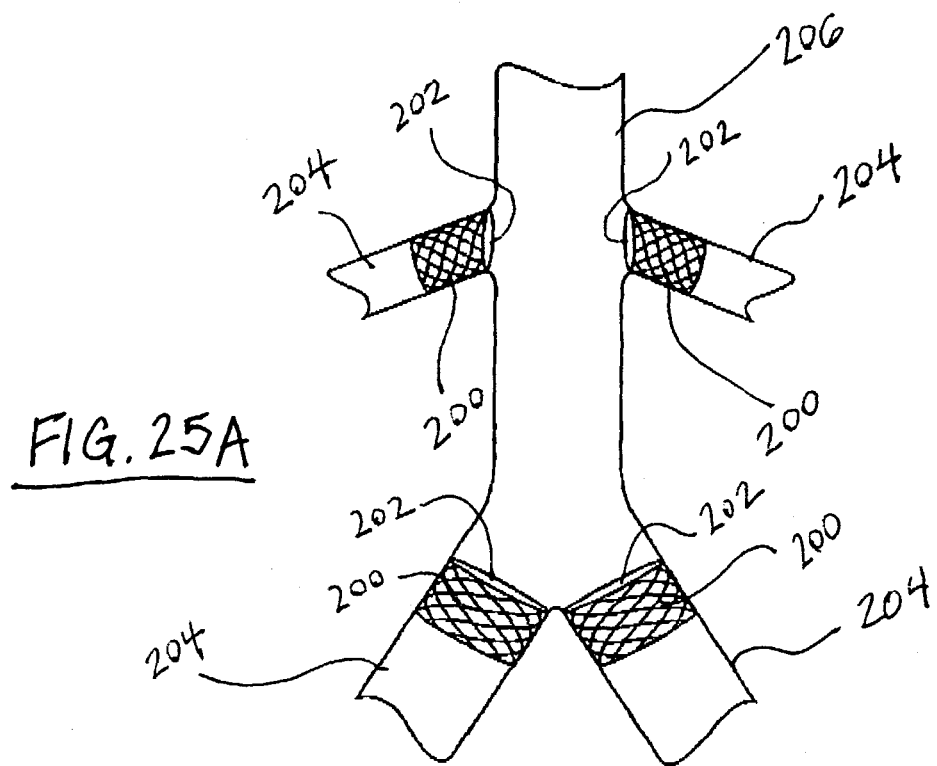
FIGS. 25A and 25B are sequential perspective views showing the device of FIGS. 24A–24B being used to secure a vascular prosthesis to a vessel.
Figure 25B:
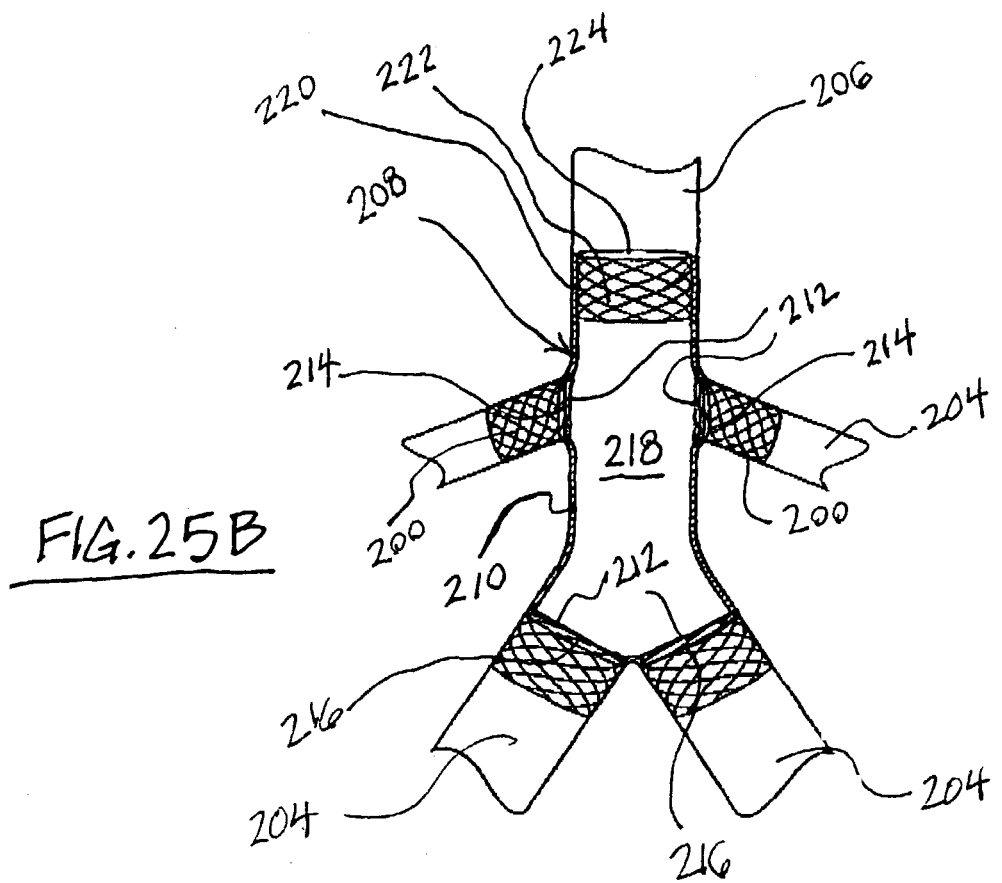

FIG. 25A shows another configuration wherein several docking members 200 are constructed and used much in the manner described above. Each docking member 200 has attachment portions 202 and is attached to a side branch 204 of the vessel 206. FIG. 25B shows the vessel 206 after a vascular prosthesis 208 has been secured to the docking members 200. The exemplary prosthesis 208 comprises a graft body 210 with attachment structure 212 provided adjacent proximal and distal openings 214, 216 of the graft. The graft attachment structure 212 is secured to complimentarily-formed attachment portions 202 of the docking members 200 to sealingly connect the graft lumen 218 with the lumens of all four side branches 204, as shown in FIG. 25B. The diseased lumen L of the vessel 206 is thereby replaced by the lumen 218 of the graft body 210.

The means for connecting the docket member attachment portions 202 and the graft attachment structures 212 may utilize magnetic force, mechanical force, or a combination of the two. In the illustrated embodiment, the docking members 200 are provided with permanent magnets configured to be coupled to corresponding permanent magnets on the prosthesis 208. In addition, a proximal end 220 of the graft body 210 is provided with an additional coupling device 222 having an opening 224, the device 222 being expanded securely against the wall of vessel 206.

FIGS. 26A–26C show for sake of example, various vascular graft configurations according to other embodiments of the invention. The illustrated grafts are suitable for use with diseased vessels with or without side branches. FIG. 26A shows a graft 230 comprising first and second portions 232, 234 which are fixed to a vessel and joined in fluid communication. The first portion 232 has attachment members 236 while the second portion 238 has attachment members 240, the use of which is explained above. The two portions 232 and 234 are attached by providing mating members 236a and 240a thereon.

FIG. 26B shows a prosthesis or graft 250 having a first portion 252 and a second portion 254 attachable thereto. The first portion 252 has multiple attachment portions 256 (including main and several side branches or lumens). The second portions 254 each have attachment portions 258 and an attachment portion 258a, the latter being securable to mating 30 portions 256a provided on two legs of the first portion 252 of the graft 250.

FIG. 26C shows a prosthesis 260 with first, second and third portions 262, 264 and 266, which are attachable to each other in a secure, sealing manner. The three portions 262, 264 and 266 of the graft 260 are respectively provided with several attachment portions 268, 270 and 272, which includes portions 268a, 270a, and 272a, for connecting the graft portions, 262, 264, and 266 to each other via securely via magnetic or mechanical means.

FIGS. 27A–27E show various docking members constructed according to additional embodiments of the invention. The docking members have an expandable body to allow engagement with a vessel wall (not shown) in order to secure the member thereto. It will be recognized that other ways of securing a docking member to a vessel may be used without departing from the principles of the present invention.

Figures 27A, 27B:
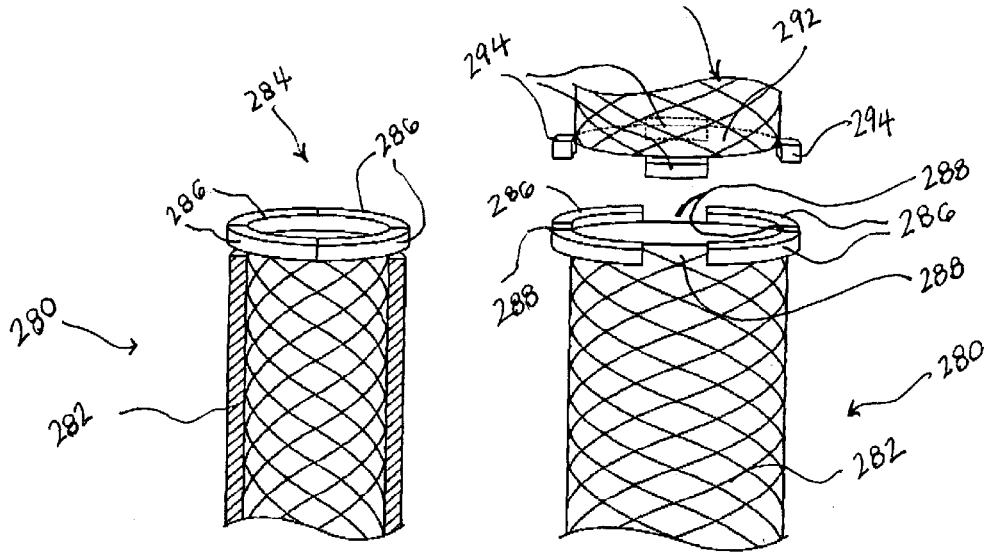
FIGS. 27A–27E are elevation views, in section, of lumen repair devices constructed according to the other embodiments of the invention.

FIG. 27A shows a docking member 280 with a collapsed body 282 and prosthesis attachment structure 284 comprising sections 206 of a suitable magnetic material. The sections 286 are relatively movable to and from the position of FIG. 27A. The body 282 of the docking members 280 is expanded to the position of FIG. 27B and into engagement with a vessel wall (not shown). This moves the sections 286 of the attachment structure 284 away from each other to the position of FIG. 27B, which forms a plurality of gaps 288 between adjacent sections 286.

FIG. 27B also shows a portion of a prosthesis such as a vascular graft 290. One end 292 of the graft 290 is provided with a plurality of attachment members 294 spaced from each other and sized to be received in the gaps 288 of the docking member sections 286. The members 294 are placed in the gaps 288 to mechanically and magnetically couple the docking member 280 and the graft 290.

Figures 27C, 27D, 27E:
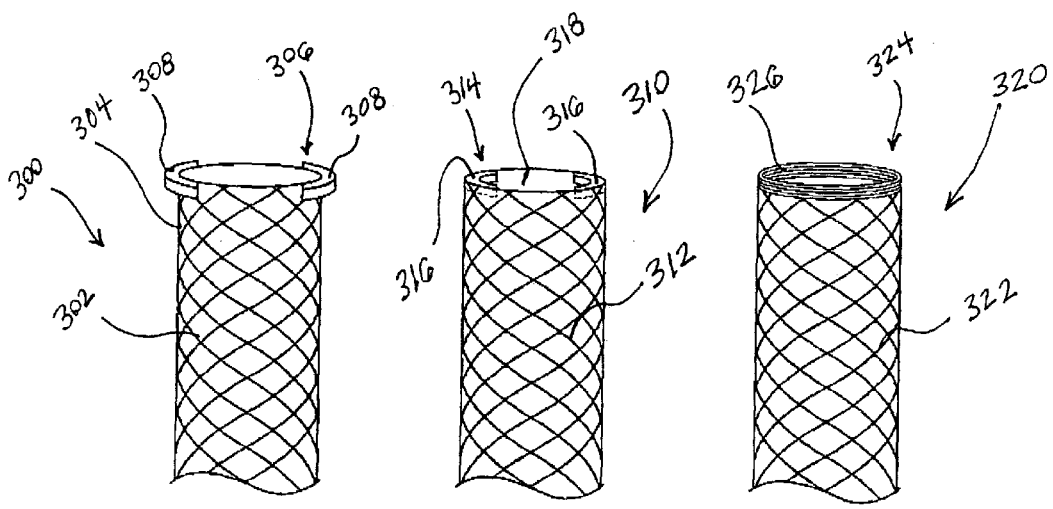

FIG. 27C shows a docking member 300 with an expandable body 302 and an end 304 provided with attachment structure 306. The attachment structure 306 comprises a plurality of sections 308 which engages corresponding structure on a graft (not shown) to fix the graft to the docking member 300, for example, via magnetic, mechanical or other means.

FIG. 27D shows a docking member 310 comprising an expandable body 312 and attachment structure 314 at one end thereof. The structure 314 is similar to the structure 306 of the previous embodiment in that it includes the plurality of spaced sections 316. The attachment sections 316, though, are disposed within the lumen 318 of the body 312 of the docking member 310. A graft (not shown) having mating attachment structures (i.e., spaced segments) is then secured to the member 310, much in the same manner as discussed above.

FIG. 27E shows a docking member 320 comprising an expandable body 322 and attachment structure 324 at an end thereof. The attachment structure 324 is in the form of ferromagnetic element 326 which may be, for example, a steel coil 326 capable of being compressed and expanded. The coiled element 326 is preferably ferromagnetic for being magnetically coupled to a graft-carried magnet (not shown).

Figure 28A:
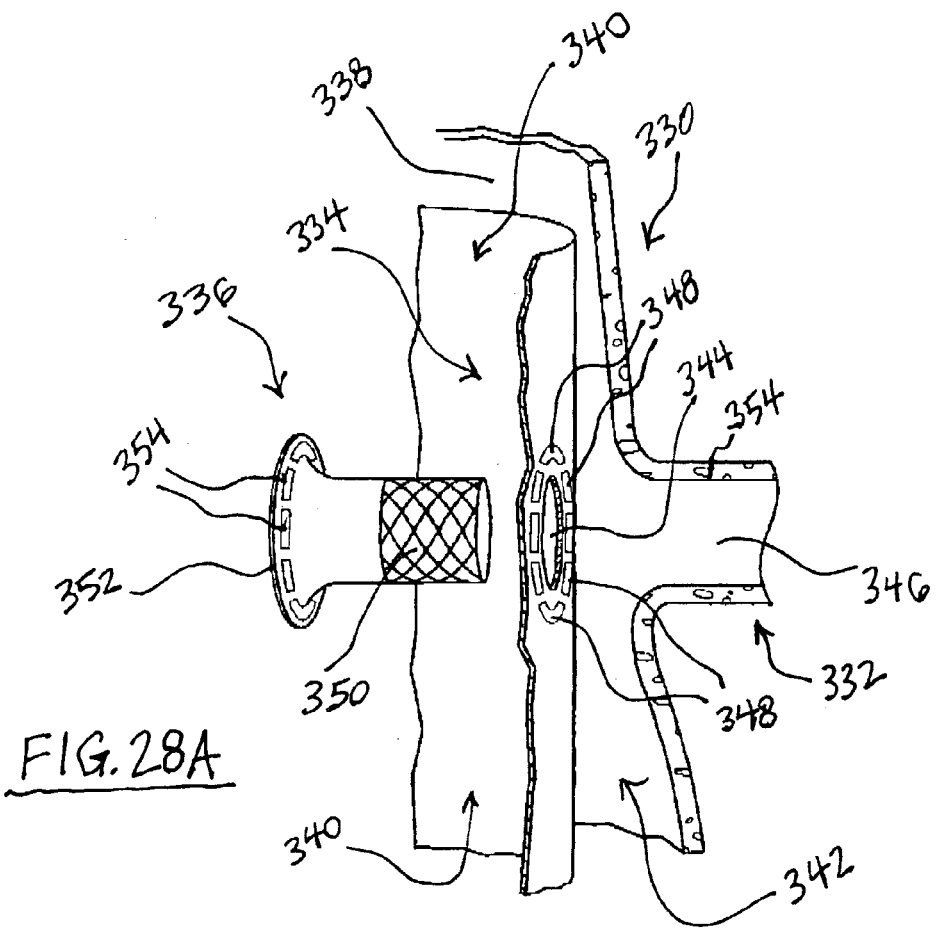
FIGS. 28A and 28B are perspective views, partially in section, showing the use of a vessel repair device constructed according to another embodiment of the invention.
Figure 28B:
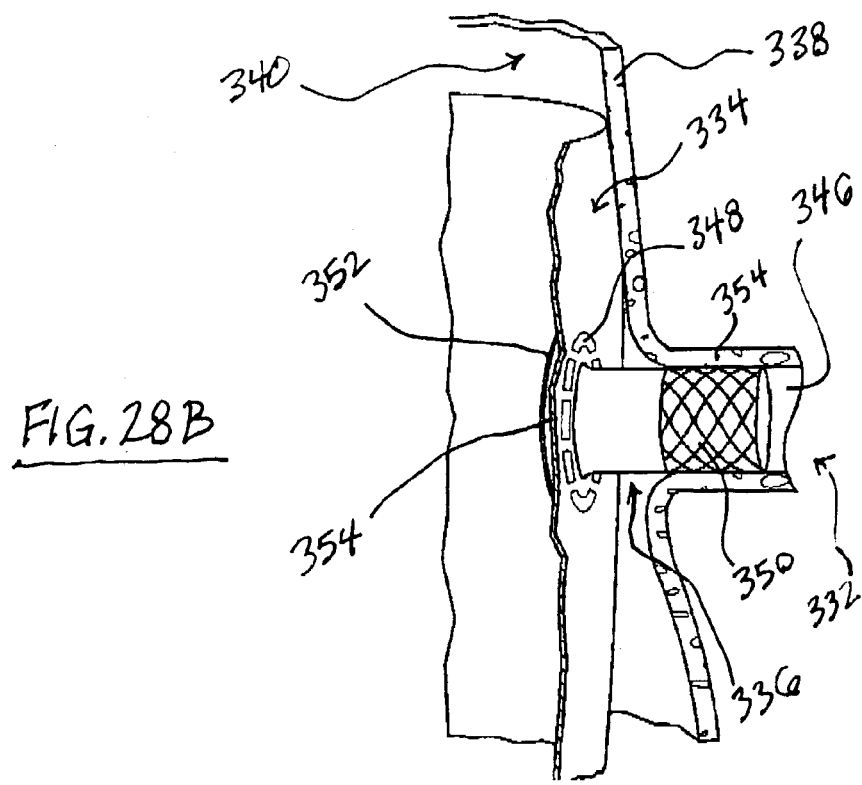

FIGS. 28A–28B show another embodiment of the invention for use in securing a prosthesis to a vessel that is diseased at or near a side branch. An exemplary vessel 330 with a side branch 332 is shown in FIG. 28A along with a prosthesis or graft 334 and a prosthesis fixation device 336. The graft 334 is preferably tubular and is configured to be secured to the wall 338 of vessel 330 such that the lumen 340 of the graft 334 replaces the diseased lumen 342 of the vessel 330.

The graft 334 has an opening 344 sized and configured for alignment with the lumen 346 of the vessel-side branch 332 once the graft 334 has been secured to the vessel 330. The area surrounding or adjacent to the 344 of graft 334 is provided with one or more attachment members 348 for securing the graft to the fixation device 336, as explained below. As shown in FIG. 28A, the fixation device 336 comprises a tubular graft body 350 with a flared end 352. The graft body 350, in whole or in part, is expandable, for example, as described above with respect to docking members of the previous embodiments. The tubular graft body 350 passes through the opening 344 in the graft 334 and is expanded against the wall 354 of the side branch 332 to secure the graft 350 to the vessels as shown in FIG. 28B.

This places the lumen 346 of the side branch 332 in sealing communication with the lumen 340 of the graft body 350, which itself is in sealing communication with the lumen 340 of the graft 334 and the lumen 342 of the vessel 330. The flared end 352 of the graft fixation device 336 includes attachment structure in the form of segments or portions 354 configured and arranged to be coupled with the attachment portions 348 provided on the graft 334 (as shown in FIG. 28B).

Figure 29A:
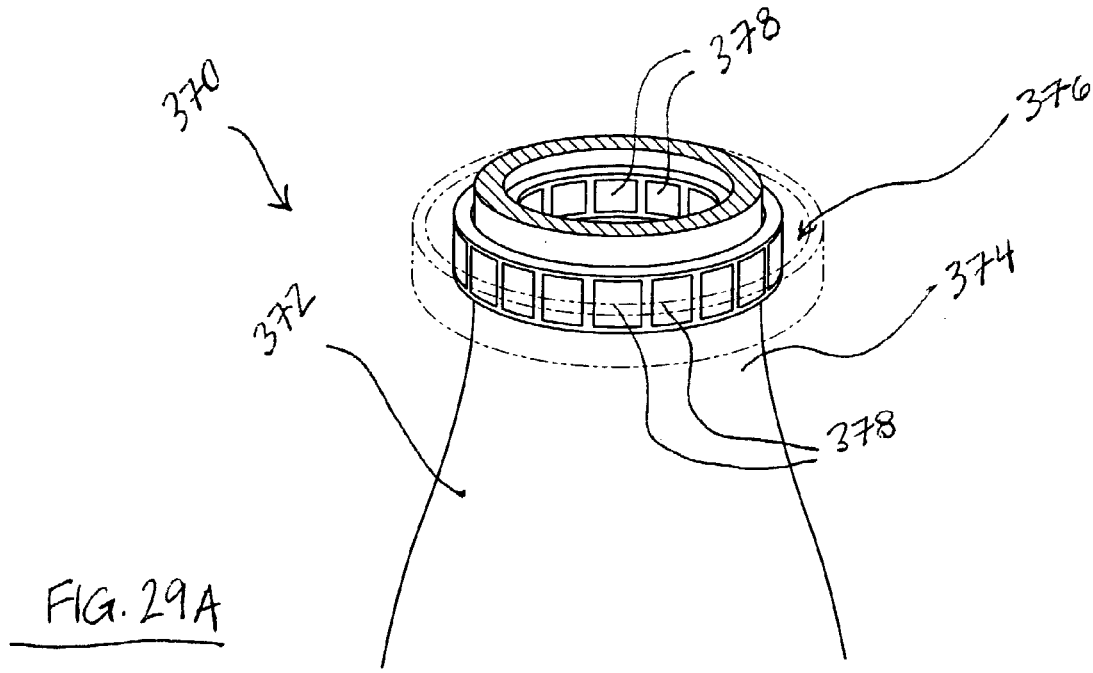
FIGS. 29A and 29B are perspective views, partially in section, showing a vessel repair device constructed according to another embodiment of the invention
Figure 29B:
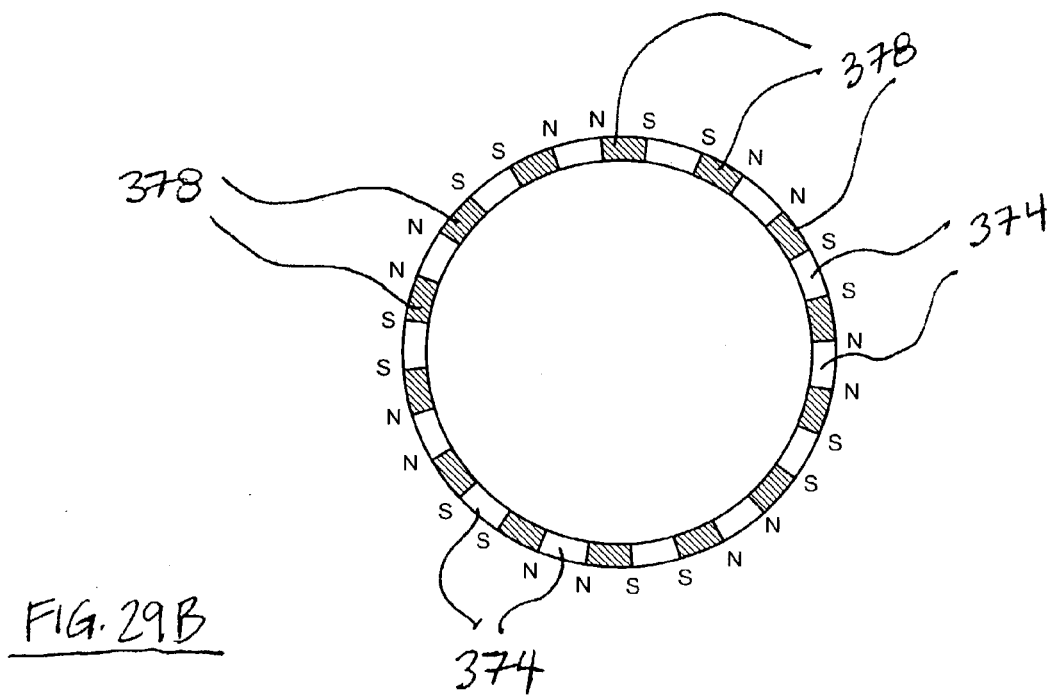

FIGS. 29A–29B show still another embodiment of the invention that provides a collapsible/expandable prosthesis or graft for use in treating a diseased vessel. The illustrated graft 370 comprises a tubular body 372 with at least one end 374 thereof provided with an attachment structure 376 for securing the graft end 374 to a docking member that has been placed in a desired position with respect to a vessel (not shown). The body 372 of the graft 370 may comprise only graft material, such as EPTFE, or graft material reinforced by suitable means, for example a stent.

FIG. 29A shows the end of 374 of the graft body 372 in its collapsed orientation. The attachment structure 376 comprises a plurality of permanent magnets 378 which, in the collapsed orientation of FIG. 29A, are disposed next to each other. The polarity of the magnets 378 is shown in FIG. 29B, which also shows the graft body 372 disposed between adjacent magnets 378. For delivery and docking the end 374 of graft 370 is collapsed (FIG. 29A) and then expanded (FIG. 29B) into engagement with corresponding attachment structure carried by the docking members. The magnets 378 repel each other such that the graft end 374 assumes the position of FIG. 29B (when unbiased). The magnets 378 place the graft in the desired position and sever to secure the graft 370 to a docking member (not shown). It will be recognized that the illustrated structure for securing a graft to a docking member represents only one of many possible constructions.

Other features, aspects and advantages of the invention beyond those specifically discussed will be apparent to those skilled in the art. Many modifications, alterations and variations of the illustrated embodiments may be made without departing from the scope and spirit of the invention as defined by the claims.

What is claimed is:

1. A method for forming an anastomosis between two blood vessels using magnetism, the method comprising the steps of:

securing a first component to a first blood vessel;

securing a second component to a side wall of a second blood vessel with an opening in the second component substantially aligned with an opening in the side wall of the second blood vessel;

placing the first component in contact with at least one of the second component and the side wall of the second blood vessel;

positioning an intimal surface of the first blood vessel adjacent an intimal surface of the second blood vessel; and using magnetism to couple the first and second components and form an anastomosis between the first and second blood vessels.

2. The method of claim 1, wherein the first component is secured to an end portion of the first blood vessel and is placed in contact with the second component.

3. The method of claim 2, wherein the first and second components are coupled to form an end-to-side anastomosis between the first and second blood vessels.

4. The method of claim 3, wherein the intimal surface of the first blood vessel extends along a length of the first component and is positioned next to the intimal surface of the side wall of the second blood vessel.

5. A method for forming an anastomosis between two blood vessels, the method comprising the steps of:

securing a first component to an end of a first blood vessel, wherein the first component and the end portion of the first blood vessel have substantially the same length and an intimal surface of the first blood vessel is uncovered by the first component;

securing a second component to a side wall of a second blood vessel with an opening in the second component substantially aligned with an opening in the side wall of the second blood vessel;

placing the first component and the end portion of the first blood vessel through the opening in the second component and the opening in the side wall of the second blood vessel, wherein the uncovered intimal surface of the first blood vessel is disposed adjacent an intimal surface of the side wall of the second blood vessel; and coupling the first and second components to form an anastomosis between the first and second blood vessels.

6. The method of claim 5, wherein the first and second components are magnetically coupled.

7. The method of claim 5, wherein the first and second components are mechanically coupled.

8. The method of claim 5, wherein the second component is sized and configured to receive the first component and the end portion of the first blood vessel so as to place respective intimal surfaces of the first and second blood vessels in close proximity to each other.

9. The method of claim 8, wherein the first component has a length that is substantially equal to the thickness of the second component combined with the thickness of the side wall of the second blood vessel.

* * * * *